US011046745B2

United States Patent
Sahin et al.

(10) Patent No.: US 11,046,745 B2
(45) Date of Patent: Jun. 29, 2021

(54) PEPTIDE MIMOTOPES OF THE CD3 T-CELL CO-RECEPTOR EPSILON CHAIN AND USES THEREOF

(71) Applicants: BioNTech SE, Mainz (DE); TRON—Translationale Onkologie an der Universitatsmedizin der Johannes Gutenberg-Universitat Mainz gGmbH, Mainz (DE); JPT Peptides Technologies GmbH, Berlin (DE)

(72) Inventors: Ugur Sahin, Mainz (DE); Laura Marie Kring, Munich (DE); Markus Fiedler, Halle an der Saale (DE); Matin Daneschdar, Budenheim (DE); Hans-Ulrich Schmoldt, Klein-Winternheim (DE); Ulf Reimer, Berlin (DE); Karsten Schnatbaum, Berlin (DE)

(73) Assignees: BioNTech SE, Mainz (DE); TRON-Translationale Onkologie an der Universitätsmedizin der Johannes Gutenberg-Universität Mainz gGmbH, Mainz (DE); JPT Peptide Technologies GmbH, Berlin (DE)

( * ) Notice: Subject to any disclaimer, the term of this patent is extended or adjusted under 35 U.S.C. 154(b) by 51 days.

(21) Appl. No.: 15/741,902

(22) PCT Filed: Jul. 14, 2015

(86) PCT No.: PCT/EP2015/066071
§ 371 (c)(1),
(2) Date: Jan. 4, 2018

(87) PCT Pub. No.: WO2017/008844
PCT Pub. Date: Jan. 19, 2017

(65) Prior Publication Data
US 2019/0070248 A1    Mar. 7, 2019

(51) Int. Cl.
| | |
|---|---|
| *A61K 38/08* | (2019.01) |
| *C07K 7/06* | (2006.01) |
| *G01N 33/566* | (2006.01) |
| *G01N 33/68* | (2006.01) |
| *C07K 14/725* | (2006.01) |
| *A61K 47/64* | (2017.01) |
| *A61K 47/66* | (2017.01) |
| *C12N 15/62* | (2006.01) |
| *A61K 38/00* | (2006.01) |

(52) U.S. Cl.
CPC .......... *C07K 14/7051* (2013.01); *A61K 38/08* (2013.01); *A61K 47/646* (2017.08); *A61K 47/66* (2017.08); *C07K 7/06* (2013.01); *C12N 15/62* (2013.01); *A61K 38/00* (2013.01); *C07K 2319/00* (2013.01); *G01N 2333/7051* (2013.01)

(58) Field of Classification Search
CPC . A61K 38/08; C07K 1/22; C07K 7/06; C07K 17/00; C07K 17/02; C07K 17/06; C07K 17/14; C07K 2319/00; G01N 33/566; G01N 33/68; G01N 2333/7051
See application file for complete search history.

(56) References Cited

FOREIGN PATENT DOCUMENTS

| EP | 2308860 | 4/2011 |
|---|---|---|
| WO | WO2005/115430 | 12/2005 |
| WO | WO2014/075697 | 5/2014 |

OTHER PUBLICATIONS

Eichler et al., "Peptides as protein binding site mimetics", Current Opinion in Chemical Biology, Current Biology Ltd., vol. 12, No. 6, 2008, 7 pages.
International Search Report and Written Opinion for PCT/EP2015/066071 dated Oct. 16, 2015, 10 pages.

*Primary Examiner* — Jeffrey E. Russel
(74) *Attorney, Agent, or Firm* — Sheppard Mullin Richter & Hampton LLP

(57) ABSTRACT

The present invention provides molecules that mimic antigenic determinants of the CD3 (cluster of differentiation 3) T-cell co-receptor epsilon chain (CD3ε). These molecules compete with CD3ε for binding to a CD3ε binding domain. e.g. a CD3ε binding domain of an antibody, and are capable of detecting antibodies against CD3ε. The mimotopes of the invention may be used to generate or inhibit immune responses in animals and preferably humans. Additionally, they may serve as tools for anti-CD3ε antibody purification and the detection of anti-CD3ε antibodies in biological samples.

38 Claims, 6 Drawing Sheets
Specification includes a Sequence Listing.

SEQUENCE LISTING

<160> NUMBER OF SEQ ID NOS: 30

<210> SEQ ID NO 1
<211> LENGTH: 207
<212> TYPE: PRT
<213> ORGANISM: Homo sapiens

<400> SEQUENCE: 1

```
Met Gln Ser Gly Thr His Trp Arg Val Leu Gly Leu Cys Leu Leu Ser
 1               5                  10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45
```

```
Cys Pro Gln Tyr Pro Gly Ser Glu Ile Leu Trp Gln His Asn Asp Lys
    50                  55                  60

Asn Ile Gly Gly Asp Glu Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
                100                 105                 110

Tyr Leu Arg Ala Arg Val Cys Glu Asn Cys Met Glu Met Asp Val Met
                115                 120                 125

Ser Val Ala Thr Ile Val Ile Val Asp Ile Cys Ile Thr Gly Gly Leu
            130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
            195                 200                 205

<210> SEQ ID NO 2
<211> LENGTH: 119
<212> TYPE: PRT
<213> ORGANISM: Artificial Sequence
<220> FEATURE:
<223> OTHER INFORMATION: Description of Artificial Sequence: Synthetic
      antibody fragment

<400> SEQUENCE: 2

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
                100                 105                 110

Thr Thr Leu Thr Val Ser Ser
        115

<210> SEQ ID NO 3
<211> LENGTH: 106
<212> TYPE: PRT
<213> ORGANISM: Artificial Sequence
<220> FEATURE:
<223> OTHER INFORMATION: Description of Artificial Sequence: Synthetic
      antibody fragment

<400> SEQUENCE: 3

Asp Ile Gln Leu Thr Gln Ser Pro Ala Ile Met Ser Ala Ser Pro Gly
1               5                   10                  15
```

Glu Lys Val Thr Met Thr Cys Arg Ala Ser Ser Val Ser Tyr Met
                20                  25                  30

Asn Trp Tyr Gln Gln Lys Ser Gly Thr Ser Pro Lys Arg Trp Ile Tyr
            35                  40                  45

Asp Thr Ser Lys Val Ala Ser Gly Val Pro Tyr Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105

<210> SEQ ID NO 4
<211> LENGTH: 119
<212> TYPE: PRT
<213> ORGANISM: Artificial Sequence
<220> FEATURE:
<223> OTHER INFORMATION: Description of Artificial Sequence: Synthetic
      antibody fragment

<400> SEQUENCE: 4

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
            115

<210> SEQ ID NO 5
<211> LENGTH: 105
<212> TYPE: PRT
<213> ORGANISM: Artificial Sequence
<220> FEATURE:
<223> OTHER INFORMATION: Description of Artificial Sequence: Synthetic
      antibody fragment

<400> SEQUENCE: 5

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
                20                  25                  30

Asn Trp Tyr Gln Gln Lys Ser Gly Thr Ser Pro Lys Arg Trp Ile Tyr
            35                  40                  45

Asp Thr Ser Lys Leu Ala Ser Gly Val Pro Ala His Phe Arg Gly Ser
        50                  55                  60

Gly Ser Gly Thr Ser Tyr Ser Leu Thr Ile Ser Gly Met Glu Ala Glu
65                  70                  75                  80

```
Asp Ala Ala Thr Tyr Tyr Cys Gln Gln Trp Ser Ser Asn Pro Phe Thr
                85                  90                  95

Phe Gly Ser Gly Thr Lys Leu Glu Ile
            100                 105

<210> SEQ ID NO 6
<211> LENGTH: 261
<212> TYPE: PRT
<213> ORGANISM: Homo sapiens

<400> SEQUENCE: 6

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
            35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
            115                 120                 125

Gly Leu Cys Ala Ile Ala Gly Val Ser Val Phe Ala Asn Met Leu Val
        130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

<210> SEQ ID NO 7
<211> LENGTH: 220
<212> TYPE: PRT
<213> ORGANISM: Homo sapiens

<400> SEQUENCE: 7

Met Ala Ser Ala Gly Met Gln Ile Leu Gly Val Val Leu Thr Leu Leu
1               5                   10                  15

Gly Trp Val Asn Gly Leu Val Ser Cys Ala Leu Pro Met Trp Lys Val
            20                  25                  30
```

```
Thr Ala Phe Ile Gly Asn Ser Ile Val Val Ala Gln Val Val Trp Glu
             35                  40                  45
Gly Leu Trp Met Ser Cys Val Val Gln Ser Thr Gly Gln Met Gln Cys
 50                  55                  60
Lys Val Tyr Asp Ser Leu Leu Ala Leu Pro Gln Asp Leu Gln Ala Ala
 65                  70                  75                  80
Arg Ala Leu Cys Val Ile Ala Leu Leu Val Ala Leu Phe Gly Leu Leu
                 85                  90                  95
Val Tyr Leu Ala Gly Ala Lys Cys Thr Thr Cys Val Glu Glu Lys Asp
                100                 105                 110
Ser Lys Ala Arg Leu Val Leu Thr Ser Gly Ile Val Phe Val Ile Ser
                115                 120                 125
Gly Val Leu Thr Leu Ile Pro Val Cys Trp Thr Ala His Ala Ile Ile
            130                 135                 140
Arg Asp Phe Tyr Asn Pro Leu Val Ala Glu Ala Gln Lys Arg Glu Leu
145                 150                 155                 160
Gly Ala Ser Leu Tyr Leu Gly Trp Ala Ala Ser Gly Leu Leu Leu Leu
                165                 170                 175
Gly Gly Gly Leu Leu Cys Cys Thr Cys Pro Ser Gly Gly Ser Gln Gly
                180                 185                 190
Pro Ser His Tyr Met Ala Arg Tyr Ser Thr Ser Ala Pro Ala Ile Ser
                195                 200                 205
Arg Gly Pro Ser Glu Tyr Pro Thr Lys Asn Tyr Val
            210                 215                 220

<210> SEQ ID NO 8
<211> LENGTH: 220
<212> TYPE: PRT
<213> ORGANISM: Homo sapiens

<400> SEQUENCE: 8

Met Ala Ser Ala Gly Met Gln Ile Leu Gly Val Val Leu Thr Leu Leu
 1               5                  10                  15
Gly Trp Val Asn Gly Leu Val Ser Cys Ala Leu Pro Met Trp Lys Val
                 20                  25                  30
Thr Ala Phe Ile Gly Asn Ser Ile Val Val Ala Gln Val Val Trp Glu
             35                  40                  45
Gly Leu Trp Met Ser Cys Val Val Gln Ser Thr Gly Gln Met Gln Cys
 50                  55                  60
Lys Val Tyr Asp Ser Leu Leu Ala Leu Pro Gln Asp Leu Gln Ala Ala
 65                  70                  75                  80
Arg Ala Leu Cys Val Ile Ala Leu Leu Val Ala Leu Phe Gly Leu Leu
                 85                  90                  95
Val Tyr Leu Ala Gly Ala Lys Cys Thr Thr Cys Val Glu Glu Lys Asp
                100                 105                 110
Ser Lys Ala Arg Leu Val Leu Thr Ser Gly Ile Val Phe Val Ile Ser
                115                 120                 125
Gly Val Leu Thr Leu Ile Pro Val Cys Trp Thr Ala His Ala Val Ile
            130                 135                 140
Arg Asp Phe Tyr Asn Pro Leu Val Ala Glu Ala Gln Lys Arg Glu Leu
145                 150                 155                 160
Gly Ala Ser Leu Tyr Leu Gly Trp Ala Ala Ser Gly Leu Leu Leu Leu
                165                 170                 175
Gly Gly Gly Leu Leu Cys Cys Thr Cys Pro Ser Gly Gly Ser Gln Gly
                180                 185                 190
```

```
Pro Ser His Tyr Met Ala Arg Tyr Ser Thr Ser Ala Pro Ala Ile Ser
        195                 200                 205

Arg Gly Pro Ser Glu Tyr Pro Thr Lys Asn Tyr Val
    210                 215                 220

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide mimotope
<220> FEATURE:
<221> NAME/KEY: MOD_RES
<222> LOCATION: (1)..(1)
<223> OTHER INFORMATION: Any amino acid, preferably an amino acid
      selected from the group consisting of Tyr, Trp, Val, Thr, Ser,
      Arg, Gln, Pro, Asn, Met, Leu, Lys, Ile, His, Gly, Phe, Glu, Asp
      and Ala
<220> FEATURE:
<221> NAME/KEY: MOD_RES
<222> LOCATION: (6)..(6)
<223> OTHER INFORMATION: Any amino acid, preferably an amino acid
      selected from the group consisting of Gly, Asp, Glu and Trp
<220> FEATURE:
<221> NAME/KEY: MOD_RES
<222> LOCATION: (9)..(9)
<223> OTHER INFORMATION: Any amino acid, preferably an amino acid
      selected from the group consisting of Gln, Tyr, Trp, Phe, Glu, Asp
      and Ala
<220> FEATURE:
<223> OTHER INFORMATION: See specification as filed for detailed
      description of substitutions and preferred embodiments

<400> SEQUENCE: 9

Xaa Cys Thr Arg Pro Xaa Asp Pro Xaa Cys
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide mimotope

<400> SEQUENCE: 10

Ala Cys Thr Arg Pro Gly Asp Pro Gln Cys
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide mimotope

<400> SEQUENCE: 11

Trp Cys Thr Arg Pro Gly Asp Pro Gln Cys
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide mimotope
```

```
<400> SEQUENCE: 12

Ala Cys Thr Arg Pro Glu Asp Pro Gln Cys
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide mimotope

<400> SEQUENCE: 13

Ala Cys Thr Arg Pro Gly Asp Pro Ala Cys
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide mimotope

<400> SEQUENCE: 14

Ala Cys Thr Arg Pro Gly Asp Pro Tyr Cys
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide mimotope

<400> SEQUENCE: 15

Ala Cys Thr Arg Pro Asp Asp Pro Gln Cys
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide mimotope

<400> SEQUENCE: 16

Ala Cys Thr Arg Pro Trp Asp Pro Gln Cys
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide mimotope

<400> SEQUENCE: 17

Ala Cys Thr Arg Pro Asp Asp Pro Glu Cys
1               5                   10

<210> SEQ ID NO 18
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide mimotope

<400> SEQUENCE: 18

Ala Cys Thr Arg Pro Asp Asp Pro Trp Cys
1               5                   10

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide mimotope
<220> FEATURE:
<221> NAME/KEY: MOD_RES
<222> LOCATION: (15)..(15)
<223> OTHER INFORMATION: K(Bio)

<400> SEQUENCE: 19

Ala Cys Thr Arg Pro Gly Asp Pro Gln Cys Gly Gly Gly Ser Lys
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide mimotope
<220> FEATURE:
<221> NAME/KEY: MOD_RES
<222> LOCATION: (15)..(15)
<223> OTHER INFORMATION: K(Bio)

<400> SEQUENCE: 20

Ala Cys Thr Arg Pro Asp Asp Pro Gln Cys Gly Gly Gly Ser Lys
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide mimotope
<220> FEATURE:
<221> NAME/KEY: MOD_RES
<222> LOCATION: (15)..(15)
<223> OTHER INFORMATION: K(Bio)

<400> SEQUENCE: 21

Trp Cys Thr Arg Pro Gly Asp Pro Gln Cys Gly Gly Gly Ser Lys
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide mimotope
<220> FEATURE:
<221> NAME/KEY: MOD_RES
<222> LOCATION: (15)..(15)
<223> OTHER INFORMATION: K(Bio)

<400> SEQUENCE: 22
```

```
Ala Cys Thr Arg Pro Glu Asp Pro Gln Cys Gly Gly Gly Ser Lys
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide mimotope
<220> FEATURE:
<221> NAME/KEY: MOD_RES
<222> LOCATION: (15)..(15)
<223> OTHER INFORMATION: K(Bio)

<400> SEQUENCE: 23

Ala Cys Thr Arg Pro Gly Asp Pro Ala Cys Gly Gly Gly Ser Lys
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide mimotope
<220> FEATURE:
<221> NAME/KEY: MOD_RES
<222> LOCATION: (15)..(15)
<223> OTHER INFORMATION: K(Bio)

<400> SEQUENCE: 24

Ala Cys Thr Arg Pro Gly Asp Pro Tyr Cys Gly Gly Gly Ser Lys
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide mimotope
<220> FEATURE:
<221> NAME/KEY: MOD_RES
<222> LOCATION: (5)..(5)
<223> OTHER INFORMATION: N-methylisoleucine
<220> FEATURE:
<221> NAME/KEY: MOD_RES
<222> LOCATION: (15)..(15)
<223> OTHER INFORMATION: K(Bio)

<400> SEQUENCE: 25

Ala Cys Thr Arg Leu Gly Asp Pro Gln Cys Gly Gly Gly Ser Lys
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide mimotope
<220> FEATURE:
<221> NAME/KEY: MOD_RES
<222> LOCATION: (15)..(15)
<223> OTHER INFORMATION: K(Bio)

<400> SEQUENCE: 26

Ala Cys Thr Arg Pro Trp Asp Pro Gln Cys Gly Gly Gly Ser Lys
1               5                   10                  15
```

```
<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide mimotope
<220> FEATURE:
<221> NAME/KEY: MOD_RES
<222> LOCATION: (15)..(15)
<223> OTHER INFORMATION: K(Bio)

<400> SEQUENCE: 27

Ala Cys Thr Arg Pro Asp Asp Pro Glu Cys Gly Gly Gly Ser Lys
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide mimotope
<220> FEATURE:
<221> NAME/KEY: MOD_RES
<222> LOCATION: (15)..(15)
<223> OTHER INFORMATION: K(Bio)

<400> SEQUENCE: 28

Ala Cys Thr Arg Pro Asp Asp Pro Trp Cys Gly Gly Gly Ser Lys
1               5                   10                  15

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide mimotope

<400> SEQUENCE: 29

Ala Cys Thr Arg Pro Gly Asp Pro Gln Cys Gly Gly Gly Ser
1               5                   10

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 30

His His His His His His
1               5
```

PEPTIDE MIMOTOPES OF THE CD3 T-CELL CO-RECEPTOR EPSILON CHAIN AND USES THEREOF

CROSS-REFERENCE TO RELATED APPLICATION

This application is a U.S. National Stage Application under 35 U.S.C. § 371 of International Application No. PCT/EP2015/066071, filed Jul. 14, 2015, the content of which is incorporated herein by reference in its entirety in the present disclosure.

SEQUENCE LISTING

The instant application contains a Sequence Listing which has been submitted electronically in ASCII format and is hereby incorporated by reference in its entirety. Said ASCII copy, created on Jun. 22, 2018, is named 60EZ-268365-US SL.txt and is 20,021 bytes in size.

The present invention provides molecules that mimic antigenic determinants of the CD3 (cluster of differentiation 3) T-cell co-receptor epsilon chain (CD3ε). These molecules compete with CD3ε for binding to a CD3ε binding domain, e.g. a CD3ε binding domain of an antibody, and are capable of detecting antibodies against CD3ε. The mimotopes of the invention may be used to generate or inhibit immune responses in animals and preferably humans. Additionally, they may serve as tools for anti-CD3ε antibody purification and the detection of anti-CD3ε antibodies in biological samples.

The CD3 (cluster of differentiation 3) T-cell co-receptor is an integral proteinaceous component of the T-cell receptor (TCR) complex and by this a key element of T-cell triggered immune responses. In mammals CD3 is composed of four distinct domains, a γ chain, a δ chain, and two ε chains. These chains associate with the TCR and the ζ-chain to generate an activation signal in T-lymphocytes.

Due to its key function in T-cell mediated immune responses CD3 is a favorable target of antibody developments (Chatenoud, L. & Bluestone, J. A., Nat. Rev. Immunol. 7, 622-632 (2007)). The CD3-specific monoclonal antibody Muromonab-CD3 (Orthoclone OKT3®) (Emmons, C. & Hunsicker, L. G., Iowa Med. 77, 78-82 (1987); Reichert, J. M., MAbs. 4, 413-415 (2012)) e.g. is approved for the therapy of acute, glucocorticoid-resistant rejection of allogeneic renal, heart and liver transplants. Others, like teplizumab or visilizumab were also tested as novel treatment opportunities for autoimmune diseases (Chatenoud, L. & Bluestone, J. A., Nat. Rev. Immunol. 7, 622-632 (2007); St Clair, E. W., Curr. Opin. Immunol. 21, 648-657 (2009)). In addition to these immunosuppressant applications, anti-CD3 antibody derived fragments were successfully used in bi- or trispecific antibody formats for cancer immunotherapy. These engineered formats simultaneously bind to a T-cell via the anti-CD3 portion and a specific target on tumor cells to be destroyed (Spiess, C., Zhai, Q., & Carter, P. J., Mol. Immunol. (2015)).

For the development of (bispecific) antibodies towards clinical use the detection and quantification of the antibody after application to animals and patients is crucial for the characterization of ADME (absorption, distribution, metabolism, and excretion) and PK (pharmacokinetics) properties. Typically, ELISA-based assays are being applied for this purpose using the corresponding antigen. Unfortunately, transmembrane proteins are often difficult to produce and handle due to their peculiar nature as membrane-embedded structures (Scott, D. J., Kummer, L., Tremmel, D., & Pluckthun, A., Curr. Opin. Chem. Biol. 17, 427-435 (2013)). This obstacle can be overcome by using anti-idiotypic antibodies which bind specifically to the antigen binding region of the therapeutic antibody. However, generating such anti-idiotypic antibodies is time-consuming and expensive. Therefore, mimotopes as easier-to-prepare structures are considered useful substitutes to mimic the full-length antigen, allowing tight specific binding of the therapeutic antibody. Mimotopes can be proteins but also oligopeptides (Casey, J. L. et al., J. Clin. Microbiol. 44, 764-771 (2006); Kieber-Emmons, T., Immunol. Res. 17, 95-108 (1998); Tang, Y. et al., J. Biol. Chem. 274, 27371-27378 (1999); Wagner, S. et al., Clin. Cancer Res. 14, 8178-8183 (2008)).

As an alternative to protein ELISA, peptide ELISA is a technique that is increasingly being used (Velumani, S. et al., PLoS. One. 6, e20737 (2011)). Peptides are easily accessible by chemical synthesis, show higher stability and are easier to handle compared to proteins. In general, peptide ELISA enables the analysis of protein/protein interactions on the amino acid sequence level, e.g. for definition of protein interaction sites.

It has been an object of the invention to prepare structures which may serve as substitutes to mimic antigenic determinants of CD3, in particular CD3ε, and which are available in a format which is compatible with biochemical formats for assay analytics and purification procedures.

In the present invention, the systematic development of peptide-based mimotopes for the T-cell co-receptor epsilon chain (CD3ε) is reported. These peptide-based mimotopes bind to the variable fragment of anti-CD3ε antibodies in the context of a whole IgG or as a part of an engineered bi- or trispecific format. The mimotope discovery and optimization process was performed via a combined screening and affinity maturation approach using phage display followed by a peptide-microarray-based characterization of the structure-activity-relationship (SAR) of the peptide hits leading to rapid optimization of their binding properties. The resulting mimotopes were shown to bind strongly and specifically to two different CD3ε specific antibodies and may serve to generate or inhibit immune responses in animals and preferably humans. Additionally, they may be applied as tools for affinity purification purposes and the detection of anti CD3ε chain antibodies or alternative antibody formats in biological samples.

The identification and isolation of molecules that mimic antigenic determinants of CD3 provides significant advantages and benefits. The use of molecules mimicking epitopes, and in particular peptide based mimotopes, as diagnostic antigens is advantageous because it allows to focus on relevant single specificities and avoids the diagnostically unimportant epitopes present in complex antigens. Peptides of high quality and stability can be cheaply and reproducibly produced and are easily applied to ELISA as well as other formats.

SUMMARY OF THE INVENTION

The present invention provides a peptide mimotope of CD3 (cluster of differentiation 3), specifically of CD3 epsilon chain (CD3ε). Specifically, the present invention provides a peptide mimotope of CD3, which comprises the amino acid sequence:

(SEQ ID NO: 9)
Xaa1 Cys Thr Arg Pro Xaa2 Asp Pro Xaa3 Cys wherein

Xaa1 is any amino acid, preferably an amino acid selected from the group consisting of Tyr, Trp, Val, Thr, Ser, Arg, Gln, Pro, Asn, Met, Leu, Lys, Ile, His, Gly, Phe, Glu, Asp and Ala, more preferably an amino acid selected from the group consisting of Tyr, Trp, Val, Thr, Ser, Arg, Gln, Pro, Asn, Met, Leu, Lys, Ile, His, Gly, Phe, Glu, and Ala, more preferably an amino acid selected from the group consisting of Tyr, Trp, Val, Thr, Ser, Arg, Pro, Met, Leu, Lys, Ile, His, Gly, Phe, Glu, and Ala, more preferably an amino acid selected from the group consisting of Tyr, Trp, Val, Thr, Ser, Arg, Pro, Leu, Ile, Gly, Phe, and Ala, Xaa2 is any amino acid, preferably an amino acid selected from the group consisting of Gly, Asp, Glu and Trp, more preferably an amino acid selected from the group consisting of Gly, Asp and Glu, and Xaa3 is any amino acid, preferably an amino acid selected from the group consisting of Gln, Tyr, Trp, Phe, Glu, Asp and Ala.

In one embodiment, the peptide mimotope comprises an amino acid sequence selected from the group consisting of:

```
                                      (SEQ ID NO: 10)
Ala Cys Thr Arg Pro Gly Asp Pro Gln Cys (SEQ ID NO: 11)
Trp Cys Thr Arg Pro Gly Asp Pro Gln Cys (SEQ ID NO: 12)
Ala Cys Thr Arg Pro Glu Asp Pro Gln Cys (SEQ ID NO: 13)
Ala Cys Thr Arg Pro Gly Asp Pro Ala Cys (SEQ ID NO: 14)
Ala Cys Thr Arg Pro Gly Asp Pro Tyr Cys (SEQ ID NO: 15)
Ala Cys Thr Arg Pro Asp Asp Pro Gln Cys (SEQ ID NO: 16)
Ala Cys Thr Arg Pro Trp Asp Pro Gln Cys (SEQ ID NO: 17)
Ala Cys Thr Arg Pro Asp Asp Pro Glu Cys (SEQ ID NO: 18)
Ala Cys Thr Arg Pro Asp Asp Pro Trp Cys
```

In one embodiment, the peptide mimotope comprises the amino acid sequence:

```
                                      (SEQ ID NO: 10)
Ala Cys Thr Arg Pro Gly Asp Pro Gln Cys.
```

In one embodiment, the peptide mimotope comprises the amino acid sequence:

```
                                      (SEQ ID NO: 15)
Ala Cys Thr Arg Pro Asp Asp Pro Gln Cys.
```

In one embodiment, the peptide mimotope comprises the amino acid sequence:

```
                                      (SEQ ID NO: 17)
Ala Cys Thr Arg Pro Asp Asp Pro Glu Cys.
```

In one embodiment, the peptide mimotope is a structural mimic of either a linear or conformational CD3 epitope. In one embodiment, the peptide mimotope is a structural mimic of an epitope in the extracellular domain of CD3.

In one embodiment, the peptide mimotope has a binding capacity to a CD3 binding domain and/or competes with CD3 for binding to a CD3 binding domain. In one embodiment, the CD3 binding domain is comprised by a binding agent to CD3. In one embodiment, the binding agent to CD3 is selected from the group consisting of an antibody or antibody fragment to CD3, or a bispecific or multispecific molecule comprising a binding domain to CD3. In one embodiment, the binding agent to CD3 is selected from the group consisting of artificial binding molecules (scaffolds) including but not limited to nanobodies, affibodies, anticalins, DARPins, monobodies, avimers, and microbodies. In one embodiment, the bispecific molecule is a bispecific antibody. In one embodiment, the bispecific antibody is a bispecific single chain antibody. In one embodiment, the binding agent binds to an epitope in the extracellular domain of CD3. In one embodiment, said binding is a specific binding.

In one embodiment, the bispecific or multispecific molecule comprises a first binding domain binding to CD3 and a second binding domain binding to a tumor cell, e.g. by binding to a tumor antigen expressed on the surface of the tumor cell.

In one embodiment, a CD3 binding domain comprises a variable domain of a heavy chain of an immunoglobulin (VH) with a specificity for CD3 (VH(CD3)) and a variable domain of a light chain of an immunoglobulin (VL) with a specificity for CD3 (VH(CD3)). In one embodiment, the VH(CD3) comprises an amino acid sequence represented by SEQ ID NO: 2 or a fragment thereof or a variant of said amino acid sequence or fragment and the VL(CD3) comprises an amino acid sequence represented by SEQ ID NO: 3 or a fragment thereof or a variant of said amino acid sequence or fragment. In one embodiment, the VH(CD3) comprises an amino acid sequence represented by SEQ ID NO: 4 or a fragment thereof or a variant of said amino acid sequence or fragment and the VL(CD3) comprises an amino acid sequence represented by SEQ ID NO: 5 or a fragment thereof or a variant of said amino acid sequence or fragment.

In one embodiment of the invention, binding is specific binding.

In one embodiment, the amino acid sequence of the peptide mimotope described above is conjugated to at least one fusion partner. In one embodiment, the amino acid sequence of the peptide mimotope is part of a fusion polypeptide. In one embodiment, the peptide mimotope further comprises at least one fusion partner. In one embodiment, the fusion partner comprises a heterologous amino acid sequence.

In one embodiment, the peptide mimotope is conjugated to at least one further moiety. In one embodiment, the peptide mimotope further comprises at least one further moiety. In one embodiment, the at least one further moiety is covalently and/or non-covalently, preferably covalently associated with the peptide mimotope or the amino acid sequence of the peptide mimotope. The at least one further moiety may be a peptidic or a non-peptidic moiety.

In one embodiment, the fusion partner or further moiety comprises a carrier protein, label, reporter, or tag. In one embodiment, the reporter is a reporter for an immunological assay. In one embodiment, the reporter is selected from the group consisting of alkaline phosphatase, horseradish peroxidase, or a fluorescent molecule.

In one embodiment, the peptide mimotope is stabilized by a covalent modification. Preferably, the modification is a cyclization. In one embodiment, cyclization is via a disulfide, a lactam, preferably a gamma-lactam, or another bridge. In one embodiment, cyclization is via a disulfide between cysteine residues in the above-described amino acid sequence of the peptide mimotope.

In one embodiment, the peptide mimotopes and amino acid sequences of peptide mimotopes described herein are comprised by a structure conferring rigidity to the peptide mimotope or amino acid sequence. For example, the peptide mimotope or amino acid sequence may be inserted into a polypeptide or protein and may form a loop of said polypeptide or protein. In one particularly preferred embodiment, the peptide mimotopes described herein are cyclic peptides and the amino acid sequences of peptide mimotopes described herein are comprised by cyclic peptides.

In one embodiment, the peptide mimotope is present in oligomeric or multimeric form. In this embodiment, two or more peptide mimotopes of the invention which may be identical or different may be linked or coupled by covalent or non-covalent bonding, such as through biotin/streptavidin. Thus, peptide mimotopes of the invention may form dimers, trimers, tetramers etc.

The present invention further provides a recombinant nucleic acid which encodes a peptide mimotope of the invention. In one embodiment, the recombinant nucleic acid is in the form of a vector or in the form of RNA.

The present invention further provides a host cell comprising a recombinant nucleic acid of the invention.

The present invention further provides a test reagent or kit comprising a peptide mimotope of the invention. In one embodiment, the test reagent or kit is a diagnostic reagent or kit. In one embodiment, the peptide mimotope is conjugated to a label. According to the invention, a label may be selected from the group consisting of a radioactive compound, a chemiluminescent compound, an electroactive compound, a fluorescent compound, and a direct particulate compound.

The test kit of the invention may further comprise at least one additional reagent for performing an immunoassay and/or instructions for use of the kit for performing an immunoassay.

The present invention further provides an assay device comprising a peptide mimotope of the invention. In one embodiment, the assay device is an enzyme-linked immunosorbent assay device. In one embodiment, the peptide mimotope is releasably or non-releasably immobilised on a solid support.

The present invention further provides a method for assaying for the presence and/or amount of CD3 in a sample comprising using the peptide mimotope of the invention. In one embodiment, the peptide mimotope is used as a competitor of the CD3, e.g. for binding to an antibody against CD3.

In particular, the present invention provides a method for determining whether a sample contains CD3 which comprises providing a monoclonal antibody against CD3, reacting the monoclonal antibody with the sample in a reaction mixture containing the peptide mimotope of the invention as a competitor, and determining whether the sample contains CD3.

The present invention also provides a method for determining whether a sample contains CD3 which comprises: (a) incubating in a reaction the sample, a monoclonal antibody against CD3, and a peptide mimotope of the invention which is a competitor of CD3 for the monoclonal antibody; (b) detecting in the reaction a complex consisting of CD3 bound by the monoclonal antibody and a complex formed by the mimotope and the monoclonal antibody; and (c) comparing an amount of each of the complexes wherein a decrease in the amount of the complex comprising the peptide mimotope indicates that the sample contains CD3.

In one embodiment of the methods of the invention, the peptide mimotope is conjugated to a label or a reporter.

The present invention further provides a method for assaying for the presence and/or amount of binding agents to CD3 such as CD3 antibodies in a sample comprising using the peptide mimotope of the invention. Preferably, the peptide mimotope is used for capturing binding agents to CD3 such as CD3 antibodies in a sample.

The present invention further provides a method for capturing binding agents to CD3 such as CD3 antibodies in a sample comprising using the peptide mimotope of the invention.

In particular, the present invention provides a method of determining CD3 antibodies in a sample which comprises contacting a sample with at least one peptide mimotope of the invention and assaying for the presence or absence of mimotope-antibody complexes, wherein the presence of mimotope-antibody complexes is indicative of the presence of CD3 antibodies in the sample.

In one embodiment, the methods of the invention are performed in the context of an immunoassay.

In one embodiment of the methods of the invention, the peptide mimotope is releasably or non-releasably immobilised on a solid support.

The present invention also provides a method of separating and/or purifying CD3 binding agents using the peptide mimotope of the invention. In this embodiment, the peptide mimotope can be used in the context of affinity chromatography. In particular, the method may comprise contacting a sample with at least one peptide mimotope of the invention and separating mimotope-CD3 binding agent complexes from other components of the sample. In one embodiment, the present invention provides a method of purifying a CD3 binding agent, comprising a step of treating a sample comprising the CD3 binding agent with an immobilized peptide mimotope of the invention, a washing step to separate off unwanted compounds such as impurities, and an elution step to obtain the CD3 binding agent.

The present invention further provides a pharmaceutical composition comprising the peptide mimotope of the invention, the recombinant nucleic acid of the invention or the host cell of the invention.

The present invention further provides a method of treating a subject comprising administering to the subject the peptide mimotope of the invention, the recombinant nucleic acid of the invention, the host cell of the invention or the pharmaceutical composition of the invention. In one embodiment, the subject is, will or has been exposed to a CD3 binding agent such as a CD3 specific antibody.

Thus, the present invention provides a method for treating a subject which is, will or has been exposed to a CD3 binding agent such as a CD3 binding agent comprising a first binding domain binding to CD3 and a second binding domain binding to a cancer cell, e.g. by binding to a tumor antigen expressed on the surface of the cancer cell, e.g. with the aim of treating cancer, in particular cancer involving cells expressing a tumor antigen, comprising treating the subject with the peptide mimotope of the invention, the recombinant nucleic acid of the invention, the host cell of the invention or the pharmaceutical composition of the invention. In one embodiment, the peptide mimotope is antagonistic to the CD3 binding agent. In one embodiment, the peptide mimotope neutralizes binding of the CD3 binding agent to CD3.

The present invention further provides the peptide mimotope of the invention, the recombinant nucleic acid of the invention, the host cell of the invention or the pharmaceutical composition of the invention for use in treating a subject, e.g. for use in the above methods of the invention.

The present invention further provides a method for eliciting antibodies against CD3 in a subject comprising treating the subject with a peptide mimotope of the invention.

In one embodiment of the invention, a reference to CD3 includes and preferably is to be considered as a reference to the epsilon chain of CD3 (CD3ε). In one embodiment of the invention, a CD3 binding domain, a binding domain to CD3, a CD3 binding agent or a binding agent to CD3 binds to the epsilon chain of CD3 (CD3ε).

In one embodiment, CD3 is expressed on the surface of a T-cell. In one embodiment, binding of a binding agent to CD3 on T-cells results in proliferation and/or activation of said T cells, wherein said activated T-cells preferably release cytotoxic factors, e.g. perforins and granzymes, and initiate cytolysis and apoptosis of cancer cells.

Other features and advantages of the instant invention will be apparent from the following detailed description and claims.

DETAILED DESCRIPTION OF THE INVENTION

Figure 1:
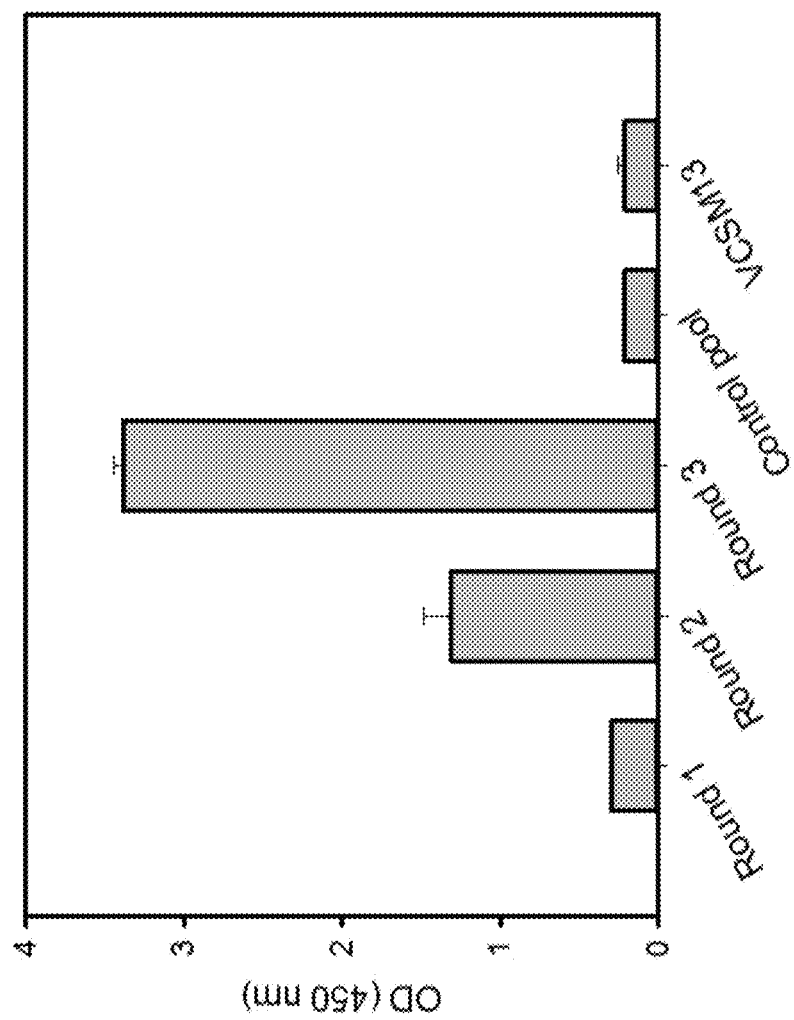
FIG. 1. Enrichment of TR66 specific phages for each round of selection, measured by an indirect phage ELISA. 10 μg of TR66 antibody were coated per well of a Nunc Maxisorp plate. After blocking 1E+12 phages of the respective pools derived from the successive screening rounds were added to each well. An unrelated phage pool and the VCSM13 wild type phages were used as controls. Binding was detected with a HRP conjugated goat anti-M13 antibody (GE Healthcare) and the chromogenic substrate 3,3',5,5'-Tetramethylbenzidine (TMB). The mean of two experiments is shown. SD values are presented as error bars.

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., *Molecular Cloning: A Laboratory Manual*, 2$^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

CD3 (cluster of differentiation 3) denotes an antigen that is expressed on mature human T-cells, thymocytes and a subset of natural killer cells as part of the multimolecular T-cell receptor (TCR) complex. The T-cell co-receptor is a protein complex and is composed of four distinct chains. In mammals, the complex contains a CD3γ chain, a CD3δ chain, and two CD3ε chains. These chains associate with a molecule known as the T-cell receptor (TCR) and the ζ-chain to generate an activation signal in T-lymphocytes. The TCR, ζ-chain, and CD3 molecules together comprise the TCR complex.

The human CD3 epsilon (CD3ε) is indicated in GenBank Accession No. NM_000733 and comprises SEQ ID NO: 1. The human CD3 gamma (CD3γ) is indicated in GenBank Accession No. NM 000073. The human CD3 delta (CD3δ) is indicated in GenBank Accession No. NM_000732. CD3 is responsible for the signal transduction of the TCR. As described by Lin and Weiss, Journal of Cell Science 114, 243-244 (2001), activation of the TCR complex by binding of MHC-presented specific antigen epitopes results in the phosphorylation of immunoreceptor tyrosine-based activation motifs (ITAMs) by Src family kinases, triggering recruitment of further kinases which results in T-cell activation including Ca$^{2+}$ release. Clustering of CD3 on T cells, e.g. by immobilized anti-CD3-antibodies, leads to T-cell activation similar to the engagement of the T cell receptor, but independent from its clone typical specificity.

As used herein, "CD3" includes human CD3 and includes an antigen that is expressed on human T cells as part of the multimolecular T-cell receptor complex. In one embodiment of the invention, a reference to CD3 includes and preferably is to be considered as a reference to the epsilon chain of CD3 (CD3ε). CD3ε has a N-terminal extracellular domain, a transmembrane domain and a cytoplasmic tail.

The term "extracellular domain" or "extracellular portion" in the context of the present invention refers to a part of a molecule such as a protein that is facing the extracellular space of a cell and preferably is accessible from the outside of said cell, e.g., by antigen-binding molecules such as antibodies located outside the cell.

The terms "portion" or "part" are used interchangeably herein and refer to a continuous or discontinuous element of a structure such as an amino acid sequence. The term "fragment" refers to a continuous element of a structure such as an amino acid sequence. A portion, part or fragment of a structure preferably comprises one or more functional properties, e.g. binding properties, of said structure. A portion or part of a protein sequence preferably comprises at least 6, in particular at least 8, at least 12, at least 15, at least 20, at least 30, at least 50, or at least 100 consecutive and/or non-consecutive amino acids of the protein sequence. A fragment of a protein sequence preferably comprises at least 6, in particular at least 8, at least 12, at least 15, at least 20, at least 30, at least 50, or at least 100 consecutive amino acids of the protein sequence According to the present invention the term "mimotope" refers to a molecule which is a mimic of an epitope. The mimotope may also act as a competitor for the epitope of which it is a mimic in in vitro assays (e.g. ELISA assays) and preferably binds to the same antigen-binding region of an antibody which binds immunospecifically to an epitope of a desired antigen. The mimotope may elicit an immunological response in a host that is reactive to the antigen of which it is a mimic.

The term "epitope" refers to an antigenic determinant in a molecule, i.e., to the part in a molecule that is recognized by the immune system, for example, that is recognized by an antibody. For example, epitopes are the discrete, three-dimensional sites on an antigen, which are recognized by the immune system. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. An epitope of a protein preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 8, 9, 10, 11, 12, 13, 14, 15, 16, 17, 18, 19, 20, 21, 22, 23, 24, or 25 amino acids in length.

According to the invention, peptide mimotopes can be synthetically produced by chemical synthesis methods which are well known in the art, either as an isolated peptide or as a part of another peptide or polypeptide. Alternatively, a peptide mimotope can be produced in a microorganism which produces the peptide mimotope which is then isolated and if desired, further purified. Thus, the peptide mimotope can be produced in microorganisms such as bacteria, yeast, or fungi; in a eukaryote cells such as mammalian or insect cells; or, in a recombinant virus vector such as adenovirus, poxvirus, herpesvirus, Simliki forest virus, baculovirus, bacteriophage, sindbis virus, or sendai virus. Suitable bacteria for producing the peptide mimotope include *Escherichia coli, Bacillus subtilis*, or any other bacterium that is capable of expressing peptides such as the peptide mimotope. Suitable yeast types for expressing the peptide mimotope include, but are not limited to *Saccharomyces cerevisiae, Schizosaccharomyces pombe, Candida*, or any other yeast capable of expressing peptides. Methods for using the aforementioned bacteria, recombinant virus vectors, or eukaryote cells to produce peptides are well known in the art.

To produce the peptide mimotope, the nucleic acid encoding the peptide mimotope is preferably in a plasmid and the nucleic acid is operably linked to a promoter which effects expression of the peptide mimotope in a microorganism. Suitable promoters include, but are not limited to, T7 phage promoter, T3 phage promoter, β-galactosidase promoter, and the Sp6 phage promoter. Methods for isolating and purifying peptides are well known in the art and include methods such as gel filtration, affinity chromatography, ion exchange chromatography, or centrifugation.

The peptide mimotopes, either by themselves or as part of a fusion peptide, can be conjugated to a heterologous peptide or protein. Such heterologous proteins include, but are not limited to, carrier proteins such as bovine serum albumin (BSA), and reporter enzymes which include, but are not limited to, horseradish peroxidase or alkaline phosphatase. Further, the peptide mimotopes or fusion peptides comprising the peptide mimotope can be chemically conjugated to fluorescent reporter molecules which include, but are not limited to, fluorescein or R-phycoerythrin. Methods for conjugating carrier proteins, enzymes, and fluorescent reporter molecules to peptides and fusion peptides are well known in the art.

To facilitate isolation of the peptide mimotope, a fusion polypeptide can be made wherein the peptide mimotope is translationally fused (covalently linked) to a heterologous tag such as a heterologous polypeptide or polyhistidine, preferably six histidine residues (SEQ ID NO: 30), which allows for the simplified recovery of the fusion polypeptide, e.g. its isolation by affinity chromatography or metal affinity chromatography, preferably nickel affinity chromatography. In some instances it can be desirable to remove the tag after purification. Therefore, it is also contemplated that the fusion polypeptide comprises a cleavage site at the junction between the peptide mimotope and the heterologous tag. The cleavage site consists of an amino acid sequence that is cleaved with an enzyme specific for the amino acid sequence at the site.

Peptide mimotopes according to the invention may also comprises an amino acid sequence for facilitating secretion of the molecule. Preferably, the secretion signal is a signal sequence that allows a sufficient passage through the secretory pathway and/or secretion into the extracellular environment. Preferably, the secretion signal sequence is cleavable and is removed from the mature peptide mimotope. The secretion signal sequence preferably is chosen with respect to the cell or organism wherein the peptide mimotope is produced in.

The peptide mimotopes described herein can be used in assays such as in immunoassays for assaying the presence or amount of CD3 or CD3 binding molecules such as CD3 antibodies, in particular the CD3 antibodies described herein. The peptide mimotopes can further be used in therapies for treating animals or humans exposed to CD3 binding molecules such as therapeutic CD3 antibodies, e.g. for modulating, in particular reducing, the activity of the CD3 binding molecule. Administration of CD3 binding molecules may be effective in inducing tolerance to allografts, in inducing immunosuppression, in preventing and treating rejection, in treating autoimmune diseases and in treating cancer.

Assays for determining the presence or amount of CD3 or CD3 antibodies may be carried out in a number of ways, including but not limited to immunodetection, and include ELISA, in particular peptide ELISA, competitive binding assays, and the like. In general, in such assays an antibody or antibody fragment is used that specifically binds the target peptide or protein and that is directly or indirectly bound to a label that provides for detection, e.g. indicator enzymes, radiolabels, fluorophores, or paramagnetic particles. The methods of the invention allow quantitative and/or qualitative evaluations, e.g., absolute and/or relative evaluations, of CD3 or CD3 antibodies.

For example, the peptide mimotopes, either alone, or as a component of a fusion polypeptide, such as conjugated to a carrier protein or fluorescent reporter molecule, are useful as standard and conjugates in immunoassays such as ELISAs and RIAS, which are used to determine whether a sample contains CD3. In such immunoassays, the use of CD3 as a control or as a competitor has been difficult. Therefore, the peptide mimotopes provide a significant advantage over CD3.

In general, the immunoassays are performed using an enzyme-linked immunosorbent assay (ELISA) embodiment.

A microtiter plate may be provided containing a plurality of wells wherein a first well or series of wells contains a monoclonal antibody against CD3 immobilized to the surface therein. A sample may be mixed with the peptide mimotope and the mixture added to the wells containing the bound monoclonal antibody. The mimotope peptide may be part of a fusion polypeptide. The CD3 in the sample and the peptide mimotope compete for binding to the monoclonal antibody. The ELISA is incubated for a time sufficient for antibody complexes to form. Afterwards, the wells are washed to remove any unbound material. The wells may then be incubated with a labeled antibody or an antibody conjugated to a reporter molecule that binds to the fusion polypeptide to form a complex which can be detected. A detectable signal from the reporter may indicate that the sample does not contain CD3 whereas an absence of a signal may indicate that the sample contains CD3 which had bound all of the monoclonal antibody, thereby preventing the peptide mimotope from binding the monoclonal antibody immobilized in the wells. When the fusion polypeptide comprises a label or reporter molecule such as a reporter enzyme such as alkaline phosphatase, the antibody-mimotope peptide complex can be detected directly without the need for a labeled antibody.

Alternatively, a microtiter plate may be provided containing a plurality of wells wherein a first well or series of wells contains the peptide mimotope, which may be conjugated to a carrier protein or fusion polypeptide, immobilized to the surface therein. Sample may be added to the wells containing the bound peptide mimotopes along with a constant amount of a monoclonal antibody against CD3. The CD3 in the sample and the peptide mimotope bound to the well surfaces compete for binding to the monoclonal antibody. The ELISA is incubated for a time sufficient for antibody complexes to form. Afterwards, the wells are washed to remove any unbound material. The amount of monoclonal antibody that is bound to the immobilized mimotope peptides in the well is determined by incubating the wells with a labeled antibody or an antibody conjugated to a reporter molecule that binds to the antibody against CD3 to form a complex that can be detected. A detectable signal from the reporter indicates the sample does not contain CD3 whereas an absence of a signal indicates that the sample contains CD3 which had bound all of the antibody against CD3, thereby preventing the antibody from binding the peptide mimotope immobilized in the wells. The intensity of the signal provides an estimate of the relative concentration of CD3 in the sample. Alternatively, the antibody against CD3 can be labeled with a reporter in which case the bound antibody can be detected directly without the need for a labeled antibody. In either case, detection is by methods well known in the art for detecting the particular reporter ligand.

Instead of an ELISA, the peptide mimotopes can be used in a radio immunoassay (RIA) for detecting CD3 in a sample. The RIA procedure may involve incubation of a monoclonal antibody against CD3, simultaneously with a solution of unknown sample or known standard, and a constant amount of radioactively labeled peptide mimotope or fusion polypeptide. After separation of the free peptide mimotope or fusion polypeptide from bound peptide mimotope or fusion polypeptide, the radioactivity in the respective fractions is determined. The concentration of CD3 in the unknown sample is determined by comparing results to a standard curve. Several known methods may be used for the separation of free from bound peptide mimotope or fusion polypeptide in the RIA. Radioactivity may be determined in a liquid scintillation counter.

According to the invention, the CD3 which is to be assayed may be expressed on the surface of a cell.

Mimotopes of the invention may also be used in methods for detecting the presence of antibodies against CD3. The design of suitable immunoassays to put these methods into effect may be subject to a great deal of variation, and a variety of these immunoassays are known in the art. Suitable immunoassay protocols may be based, for example, upon competition, or direct reaction, or sandwich type assays. The immunoassay protocols used may also, for example, use solid supports, or may be by immunoprecipitation. Assays may involve the use of labelled antibodies and the labels may be, for example, fluorescent, chemiluminescent, radioactive, or dye molecules. Particular preferred assays are enzyme-labelled and mediated immunoassays, such as ELISA assays.

Accordingly, the peptide mimotopes may also be used in an assay such as an ELISA assay to determine antibody against CD3 in a sample. For this purpose, the wells of ELISA plates may be coated with peptide mimotopes. Subsequently, a sample such as plasma may be added and the detection of peptide specific antibodies (primary antibody) may be performed with a labelled secondary antibody directed against the primary antibody.

Mimotopes of the invention may be bound to a solid support, for example the surface of an immunoassay well or dipstick, and/or packaged into kits in a suitable container along with suitable reagents, controls, instructions and the like.

Accordingly the present invention also provides a kit comprising at least one mimotope of the present invention. In a preferred embodiment, the kit further comprises at least one additional agent such as one or more suitable reagents for performing an immunoassay, a control, or instructions for use of the kit.

When used as an assay reagent as described herein, a mimotope of the invention may be conjugated to a label. Preferably, the label is any entity the presence of which can be readily detected. Preferably the label is a direct label. Direct labels are entities which, in their natural state, are readily visible either to the naked eye, or with the aid of an optical filter and/or applied stimulation, e.g. UV light to promote fluorescence. Examples include radioactive, chemiluminescent, electroactive (such as redox labels), and fluorescent compounds. Direct particulate labels, such as dye sols, metallic sols (e.g. gold) and coloured latex particles, are also very suitable and are, along with fluorescent compounds, preferred. Of these options, coloured latex particles and fluorescent compounds are most preferred. Concentration of the label into a small zone or volume should give rise to a readily detectable signal, e.g. a strongly coloured area. Indirect labels, such as enzymes, e.g. alkaline phosphatase and horseradish peroxidase, can also be used, although these usually require the addition of one or more developing reagents such as substrates before a visible signal can be detected.

According to the invention, a label may function to: (i) provide a detectable signal; (ii) interact with a second label to modify the detectable signal provided by the first or second label, e.g. FRET (Fluorescence Resonance Energy Transfer); (iii) affect mobility, e.g. electrophoretic mobility, by charge, hydrophobicity, shape, or other physical parameters, or (iv) provide a capture moiety, e.g., affinity, antibody/antigen, or ionic complexation. Suitable as label are structures, such as fluorescent labels, luminescent labels, chromophore labels, radioisotopic labels, isotopic labels, preferably stable isotopic labels, isobaric labels, enzyme labels, particle labels, in particular metal particle labels, magnetic particle labels, polymer particle labels, small organic molecules such as biotin, ligands of receptors or binding molecules such as cell adhesion proteins or lectins, label-sequences comprising nucleic acids and/or amino acid residues which can be detected by use of binding agents, etc. Labels comprise, in a nonlimiting manner, barium sulfate, iocetamic acid, iopanoic acid, calcium ipodate, sodium diatrizoate, meglumine diatrizoate, metrizamide, sodium tyropanoate and radio diagnostic, including positron emitters such as fluorine-18 and carbon-11, gamma emitters such as iodine-123, technetium-99m, iodine-131 and indium-111, nuclides for nuclear magnetic resonance, such as fluorine and gadolinium.

Conjugation of the label to the mimotope of the invention can be by covalent or non-covalent (including hydrophobic) bonding, or by adsorption. Techniques for such conjugation are commonplace in the art and may be readily adapted for the particular reagents employed.

According to the invention there is further provided an assay device comprising at least one mimotope of the present invention. In one embodiment, the assay device is selected from the group consisting of an enzyme-linked immunosorbent assay device.

Such a device can take different forms, and it can be varied depending on the precise nature of the assay being performed. For example, the mimotope of the invention may be coated onto a solid support, typically nitrocellulose or other hydrophobic porous material. Alternatively, the mimotope may be coated on a synthetic plastics material, microtiter assay plate, microarray chip, latex bead, filter comprising a cellulosic or synthetic polymeric material, glass or plastic slide, dipstick, capillary fill device and the like. Coating of the mimotopes to these surfaces can be accomplished by methods known in the art. Protein carriers are typically used for complexing, with BSA or adhesive peptides being the most preferred. In one embodiment, the mimotope of the invention is releasably immobilised on the solid support. In a further preferred embodiment, the diagnostic reagent is nonreleasably immobilised on the solid support.

The term "enzyme-linked immunosorbent assay or ELISA", as used herein, relates to a method for quantitatively or semi-quantitatively determining protein concentrations from a sample, e.g. blood plasma, serum or cell/tissue extracts, in a multi-well plate format (usually 96-wells per plate). Broadly, proteins in solution are adsorbed to ELISA plates. Antibodies specific for the protein of interest may be used to probe the plate. Background is minimized by optimizing blocking and washing methods (as for IHC), and specificity is ensured via the presence of positive and negative controls. Detection methods are usually colorimetric or chemiluminescence based.

The term "sample", as used herein, includes any sample which may be used for analysis purposes such as a biological sample which may be isolated from a patient. Said sample may be a body fluid sample, a tissue sample, or a cell sample. For example, samples encompassed by the present invention are tissue (e.g. section or explant) samples, single cell samples, cell colony samples, cell culture samples, blood (e.g. whole blood or blood fraction such as blood cell fraction, serum or plasma) samples, urine samples, or samples from other peripheral sources. Said samples may be mixed or pooled, e.g. a sample may be a mixture of a blood sample and a urine sample. Said samples may be provided by removing a body fluid, cell(s), cell colonies, an explant, or a section from a patient, but may also be provided by using a previously isolated sample. For example, a tissue sample may be removed from a patient by conventional biopsy techniques or a blood sample may be taken from a patient by conventional blood collection techniques. The sample, e.g. tissue sample or blood sample, may be obtained from a patient prior to initiation of the therapeutic treatment, during the therapeutic treatment, and/or after the therapeutic treatment.

In one embodiment, the sample is a body fluid sample. The term "body fluid sample", as used herein, refers to any liquid sample derived from the body of a patient. Said body fluid sample may be a blood sample, urine sample, sputum sample, breast milk sample, cerebrospinal fluid (CSF) sample, cerumen (earwax) sample, endolymph sample, perilymph sample, gastric juice sample, mucus sample, peritoneal fluid sample, pleural fluid sample, saliva sample, sebum (skin oil) sample, semen sample, sweat sample, tears sample, vaginal secretion sample, or vomit sample including components or fractions thereof. Said body fluid samples may be mixed or pooled. Thus, a body fluid sample may be a mixture of a blood and a urine sample or a mixture of a blood and cerebrospinal fluid sample. Said body fluid sample may be provided by removing a body liquid from a patient, but may also be provided by using previously isolated body fluid sample material.

In one preferred embodiment, the sample is a whole blood sample or a blood fraction sample such as a blood cell fraction, blood serum, or blood plasma sample.

The mimotopes of the invention may be further used as vaccines so as to induce CD3 antibodies or for modulating the activity of CD3 binding agents such as CD3 antibodies, in particular bispecific antibodies binding to CD3. To this end, the mimotopes of the invention may be combined with various components to produce pharmaceutically acceptable compositions.

According to the invention, the term "binding agent to CD3" or "CD3 binding agent" includes any compound that has a binding capacity to CD3, i.e. the ability of binding to an epitope present in CD3, preferably an epitope located within the extracellular domain of CD3. Preferably, such binding agent comprises at least one binding domain for CD3. The term includes molecules such as antibodies and antibody fragments, and bispecific or multispecific molecules. The term also includes all artificial binding molecules (scaffolds) having a binding capacity to CD3 including but not limited to nanobodies, affibodies, anticalins, DARPins, monobodies, avimers, and microbodies. In one particularly preferred embodiment, a CD3 binding agent is a CD3 specific antibody, preferably a CD3 specific antibody selected from the group consisting of OKT3 and TR66.

According to the invention, the term "binding domain to CD3" or "CD3 binding domain" includes the portion of a CD3 binding agent that has a binding capacity to CD3, i.e. the ability of binding to an epitope present in CD3, preferably an epitope located within the extracellular domain of CD3. For example, the term includes the antigen-binding portion of a CD3 specific antibody.

In one embodiment, a CD3 binding domain or CD3 binding agent binds to an extracellular domain of CD3. In one embodiment, a CD3 binding domain or CD3 binding agent binds to native epitopes of CD3 present on the surface of living cells. Preferably, a CD3 binding domain or CD3 binding agent is specific for CD3. Preferably, a CD3 binding domain or CD3 binding agent binds to CD3 expressed on the cell surface. In particular preferred embodiments, a CD3 binding domain or CD3 binding agent binds to native epitopes of CD3 present on the surface of living cells.

In one embodiment of the invention, a CD3 binding domain or a CD3 binding agent recognizes or binds to the epsilon chain of CD3 (CD3ε). In one embodiment of the invention, a CD3 binding domain or a CD3 binding agent is capable of specifically recognizing human CD3 epsilon in a native or near native conformation, e.g. in the context of other TCR subunits, e.g. in mouse T cells transgenic for human CD3 epsilon.

In one embodiment, a CD3 binding domain or CD3 binding agent according to the invention recognizes, i.e. binds to, the same or essentially the same epitope as a CD3 binding domain or CD3 binding agent described herein, e.g. a CD3 specific antibody selected from the group consisting of OKT3 and TR66, and/or competes with said CD3 binding domain or CD3 binding agent for binding to CD3. In one particularly preferred embodiment, a CD3 binding domain or CD3 binding agent according to the invention recognizes, i.e. binds to, the same or essentially the same epitope as OKT3 and/or TR66, and/or competes with OKT3 and/or TR66 for binding to CD3.

In one embodiment, a CD3 binding domain or a CD3 binding agent comprises a variable domain of a heavy chain of an immunoglobulin (VH) with a specificity for CD3 (VH(CD3)) and a variable domain of a light chain of an immunoglobulin (VL) with a specificity for CD3 (VL(CD3)).

In a preferred embodiment, the VH and VL regions of a CD3 binding domain or CD3 binding agent are derived from a CD3 specific antibody selected from the group consisting of OKT3 and TR66.

In one embodiment, the VH(CD3) comprises an amino acid sequence represented by SEQ ID NO: 2 or a fragment thereof or a variant of said amino acid sequence or fragment and the VL(CD3) comprises an amino acid sequence represented by SEQ ID NO: 3 or a fragment thereof or a variant of said amino acid sequence or fragment.

In one embodiment the VH(CD3) comprises an amino acid sequence represented by SEQ ID NO: 4 or a fragment thereof or a variant of said amino acid sequence or fragment and the VL(CD3) comprises an amino acid sequence represented by SEQ ID NO: 5 or a fragment thereof or a variant of said amino acid sequence or fragment.

The term "fragment" refers, in particular, to one or more of the complementarity-determining regions (CDRs), preferably at least the CDR3 variable region, of the heavy chain variable region (VH) and/or of the light chain variable region (VL). In one embodiment said one or more of the complementarity-determining regions (CDRs) are selected from a set of complementarity-determining regions CDR1, CDR2 and CDR3. In a particularly preferred embodiment, the term "fragment" refers to the complementarity-determining regions CDR1, CDR2 and CDR3 of the heavy chain variable region (VH) and/or of the light chain variable region (VL).

In one embodiment a CD3 binding domain or a CD3 binding agent comprising one or more CDRs, a set of CDRs or a combination of sets of CDRs as described herein comprises said CDRs together with their intervening framework regions. Preferably, the portion will also include at least about 50% of either or both of the first and fourth framework regions, the 50% being the C-terminal 50% of the first framework region and the N-terminal 50% of the fourth framework region. Construction of binding agents made by recombinant DNA techniques may result in the introduction of residues N- or C-terminal to the variable regions encoded by linkers introduced to facilitate cloning or other manipulation steps, including the introduction of linkers to join variable regions of the invention to further protein sequences including immunoglobulin heavy chains, other variable domains (for example in the production of diabodies) or protein labels.

In one embodiment a binding agent comprising one or more CDRs, a set of CDRs or a combination of sets of CDRs as described herein comprises said CDRs in a human antibody framework.

The term "antibody" refers to a glycoprotein comprising at least two heavy (H) chains and two light (L) chains inter-connected by disulfide bonds. The term "antibody" includes monoclonal antibodies, recombinant antibodies, human antibodies, humanized antibodies and chimeric antibodies. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "monoclonal antibody" as used herein refers to a preparation of antibody molecules of single molecular composition. A monoclonal antibody displays a single binding specificity and affinity. In one embodiment, the monoclonal antibodies are produced by a hybridoma which includes a B cell obtained from a non-human animal, e.g., mouse, fused to an immortalized cell.

The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "human antibody", as used herein, is intended to include antibodies having variable and constant regions derived from human germline immunoglobulin sequences. Human antibodies may include amino acid residues not encoded by human germline immunoglobulin sequences (e.g., mutations introduced by random or site-specific mutagenesis in vitro or by somatic mutation in vivo).

The term "humanized antibody" refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen binding sites may be wild-type or modified by one or more amino acid substitutions, e.g. modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another. Typically the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human, is less likely to elicit an immune response from a human subject when the antibodies are injected than would the constant region from a non human source. However the definition is not limited to this particular example.

Antibodies may be derived from different species, including but not limited to mouse, rat, rabbit, guinea pig and human.

Antibodies described herein include IgA such as IgA1 or IgA2, IgG1, IgG2, IgG3, IgG4, IgE, IgM, and IgD antibodies. In various embodiments, the antibody is an IgG1 antibody, more particularly an IgG1, kappa or IgG1, lambda isotype (i.e. IgG1, κ, λ), an IgG2a antibody (e.g. IgG2a, κ, λ), an IgG2b antibody (e.g. IgG2b, κ, λ), an IgG3 antibody (e.g. IgG3, κ, λ) or an IgG4 antibody (e.g. IgG4, κ, λ).

As used herein, a "heterologous antibody" is defined in relation to a transgenic organism producing such an antibody. This term refers to an antibody having an amino acid sequence or an encoding nucleic acid sequence corresponding to that found in an organism not consisting of the transgenic organism, and being generally derived from a species other than the transgenic organism.

As used herein, a "heterohybrid antibody" refers to an antibody having light and heavy chains of different organismal origins. For example, an antibody having a human heavy chain associated with a murine light chain is a heterohybrid antibody.

As used herein, "isotype" refers to the antibody class (e.g., IgM or IgG1) that is encoded by heavy chain constant region genes.

As used herein, "isotype switching" refers to the phenomenon by which the class, or isotype, of an antibody changes from one Ig class to one of the other Ig classes.

The term "rearranged" as used herein refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin (antibody) gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

Antibodies can be produced by a variety of techniques, including conventional monoclonal antibody methodology, e.g., the standard somatic cell hybridization technique of Kohler and Milstein, Nature 256: 495 (1975). Although somatic cell hybridization procedures are preferred, in principle, other techniques for producing monoclonal antibodies can be employed, e.g., viral or oncogenic transformation of B-lymphocytes or phage display techniques using libraries of antibody genes.

The preferred animal system for preparing hybridomas that secrete monoclonal antibodies is the murine system. Hybridoma production in the mouse is a very well established procedure. Immunization protocols and techniques for isolation of immunized splenocytes for fusion are known in the art. Fusion partners (e.g., murine myeloma cells) and fusion procedures are also known.

Other preferred animal systems for preparing hybridomas that secrete monoclonal antibodies are the rat and the rabbit system (e.g. described in Spieker-Polet et al., Proc. Natl. Acad. Sci. U.S.A. 92:9348 (1995), see also Rossi et al., Am. J. Clin. Pathol. 124: 295 (2005)).

To generate antibodies, mice can be immunized with carrier-conjugated peptides derived from the antigen sequence, i.e. the sequence against which the antibodies are to be directed, an enriched preparation of recombinantly expressed antigen or fragments thereof and/or cells expressing the antigen, as described. Alternatively, mice can be immunized with DNA encoding the antigen or fragments thereof. In the event that immunizations using a purified or enriched preparation of the antigen do not result in antibodies, mice can also be immunized with cells expressing the antigen, e.g., a cell line, to promote immune responses.

The immune response can be monitored over the course of the immunization protocol with plasma and serum samples being obtained by tail vein or retroorbital bleeds. Mice with sufficient titers of immunoglobulin can be used for fusions. Mice can be boosted intraperitonealy or intravenously with antigen expressing cells 3 days before sacrifice and removal of the spleen to increase the rate of specific antibody secreting hybridomas.

To generate hybridomas producing monoclonal antibodies, splenocytes and lymph node cells from immunized mice can be isolated and fused to an appropriate immortalized cell line, such as a mouse myeloma cell line. The resulting hybridomas can then be screened for the production of antigen-specific antibodies. Individual wells can then be screened by ELISA for antibody secreting hybridomas. By Immunofluorescence and FACS analysis using antigen expressing cells, antibodies with specificity for the antigen can be identified. The antibody secreting hybridomas can be replated, screened again, and if still positive for monoclonal antibodies can be subcloned by limiting dilution. The stable subclones can then be cultured in vitro to generate antibody in tissue culture medium for characterization.

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332: 323-327; Jones, P. et al. (1986) Nature 321: 522-525; and Queen, C. et al. (1989) Proc. Natl. Acad. Sci. U.S. 86: 10029-10033). Such framework sequences can be obtained from public DNA databases that include germline antibody gene sequences. These germline sequences will differ from mature antibody gene sequences because they will not include completely assembled variable genes, which are formed by V (D) J joining during B cell maturation. Germline gene sequences will also differ from the sequences of a high affinity secondary repertoire antibody at individual evenly across the variable region.

The terms "antigen-binding portion" of an antibody (or simply "binding portion") or "antigen-binding fragment" of an antibody (or simply "binding fragment") or similar terms refer to one or more fragments of an antibody that retain the ability to specifically bind to an antigen. Such antigen-binding portion is included by the term "antigen-binding domain". It has been shown that the antigen-binding function of an antibody can be performed by fragments of a full-length antibody. Examples of binding fragments encompassed within the term "antigen-binding portion" of an antibody include (i) Fab fragments, monovalent fragments consisting of the VL, VH, CL and CH domains; (ii) F(ab')$_2$ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding fragment" of an antibody. A further example is binding-domain immunoglobulin fusion proteins comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

The term "binding domain" characterizes in connection with the present invention a structure, e.g. of an antibody, which binds to/interacts with a given target structure/antigen/epitope. Thus, the binding domain according to the invention designates an "antigen-interaction-site".

All antibodies and derivatives of antibodies such as antibody fragments as described herein for the purposes of the invention are encompassed by the term "antibody". The term "antibody derivatives" refers to any modified form of an antibody, e.g., a conjugate of the antibody and another agent or antibody, or an antibody fragment. Furthermore, the antibodies and derivatives of antibodies as described herein are useful for producing binding agents of the invention such as antibody fragments.

Naturally occurring antibodies are generally monospecific, i.e. they bind to a single antigen. The present invention also envisions binding agents which are bispecific or multispecific molecules binding to CD3 and to one or more further antigens. Particularly preferred are binding agents binding to a cytotoxic cell (e.g. by engaging the CD3 receptor) and a cancer cell (by engaging a tumor antigen). Such binding agents are at least bispecific or multispecific such as trispecific, tetraspecific and so on.

Thus, in one embodiment, a binding agent according to the invention comprises at least two binding domains, wherein a first binding domain binds to CD3 and a second binding domain binds to a tumor antigen. Such binding agent may bind to a cytotoxic cell (e.g. by engaging the CD3 receptor) and a cancer cell expressing a tumor antigen to be destroyed as a target.

The bispecific or multispecific binding agent may be in the format of an antibody molecule or of an antibody-like molecule or of a protein scaffold with antibody-like properties or of a cyclic peptide with at least two binding specificities. Thus, the binding agent may comprise one or more antibodies as described herein or fragments thereof.

According to the invention, a bispecific molecule, in particular a bispecific protein, such as a bispecific antibody is a molecule that has two different binding specificities and thus may bind to two different types of antigen such as CD3 and a tumor antigen. Particularly, the term "bispecific antibody" as used herein refers to an antibody comprising two antigen-binding sites, a first binding site having affinity for a first antigen or epitope and a second binding site having binding affinity for a second antigen or epitope distinct from the first. In particular, a bispecific antibody is an artificial protein that is composed of fragments of two different antibodies (said fragments of two different antibodies forming two binding domains) and consequently binds to two different types of antigen. A bispecific antibody preferably is engineered to simultaneously bind to an immune cell, such as an immune effector cell, in particular a T cell such as a cytotoxic cell (e.g. by binding to CD3) and a target cell like a cancer cell (by binding to the tumor-associated antigen) to be destroyed.

The term "bispecific antibody" also includes diabodies. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90: 6444-6448; Poljak, R. J., et al. (1994) Structure 2: 1121-1123).

"Multispecific binding agents" are molecules which have more than two different binding specificities.

Particularly preferred according to the invention are bispecific antibodies including bispecific antibody fragments, in particular bispecific single chain antibodies including bispecific single chain antibody fragments. The term "bispecific single chain antibody" denotes a single polypeptide chain comprising two binding domains. In particular, the term "bispecific single chain antibody" or "single chain bispecific antibody" or related terms in accordance with the present invention preferably mean antibody constructs resulting from joining at least two antibody variable regions in a single polypeptide chain devoid of the constant and/or Fc portion(s) present in full immunoglobulins.

For example, a bispecific single chain antibody may be a construct with a total of two antibody variable regions, for example two VH regions, each capable of specifically binding to a separate antigen, and connected with one another through a short polypeptide spacer such that the two antibody variable regions with their interposed spacer exist as a single contiguous polypeptide chain. Another example of a bispecific single chain antibody may be a single polypeptide chain with three antibody variable regions. Here, two antibody variable regions, for example one VH and one VL, may make up an scFv, wherein the two antibody variable regions are connected to one another via a synthetic polypeptide linker, the latter often being genetically engineered so as to be minimally immunogenic while remaining maximally resistant to proteolysis. This scFv is capable of specifically binding to a particular antigen, and is connected to a further antibody variable region, for example a VH region, capable of binding to a different antigen than that bound by the scFv. Yet another example of a bispecific single chain antibody may be a single polypeptide chain with four antibody variable regions. Here, the first two antibody variable regions, for example a VH region and a VL region, may form one scFv capable of binding to one antigen, whereas the second VH region and VL region may form a second scFv capable of binding to another antigen. Within a single contiguous polypeptide chain, individual antibody variable regions of one specificity may advantageously be separated by a synthetic polypeptide linker, whereas the respective scFvs may advantageously be separated by a short polypeptide spacer as described above.

According to one embodiment of the invention, the first binding domain of the bispecific antibody comprises one antibody variable domain, preferably a VHH domain. According to one embodiment of the invention, the first binding domain of the bispecific antibody comprises two antibody variable domains, preferably a scFv, i.e. VH-VL or VL-VH. According to one embodiment of the invention, the second binding domain of the bispecific antibody comprises one antibody variable domain, preferably a VHH domain. According to one embodiment of the invention, the second binding domain of the bispecific antibody comprises two antibody variable domains, preferably a scFv, i.e. VH-VL or VL-VH. In its minimal form, the total number of antibody variable regions in the bispecific antibody according to the invention is thus only two. For example, such an antibody could comprise two VH or two VHH domains.

According to one embodiment of the invention, the first binding domain and the second binding domain of the bispecific antibody each comprise one antibody variable domain, preferably a VHH domain. According to one embodiment of the invention, the first binding domain and the second binding domain of the bispecific antibody each comprise two antibody variable domains, preferably a scFv, i.e. VH-VL or VL-VH. In this embodiment, the binding agent of the invention preferably comprises (i) a heavy chain variable domain (VH) of a CD3 antibody, (ii) a light chain variable domain (VL) of a CD3 antibody, (iii) a heavy chain variable domain (VH) of an antibody to a second antigen, e.g. of a tumor antigen specific antibody and (iv) a light chain variable domain (VL) of an antibody to a second antigen, e.g. of a tumor antigen specific antibody.

Bispecific full-length antibodies may be obtained by covalently linking two monoclonal antibodies or by conventional hybrid-hybridoma techniques. Covalent linking of two monoclonal antibodies is described in Anderson, Blood 80 (1992), 2826-34. In the context of this invention, one of the antibodies may be specific for CD3 and the other one for a tumor antigen.

In one embodiment, the bispecific molecules according to the invention comprises two Fab regions, e.g. one being directed against CD3 and the other being directed against a tumor antigen. In one embodiment, the molecule is an antigen binding fragment (Fab)2 complex. The Fab2 complex is composed of two Fab fragments, one Fab fragment comprising a Fv domain, i.e. VH and VL domains, e.g. specific for a CD3 antigen, and the other Fab fragment comprising a Fv domain specific for a tumor antigen. Each of the Fab fragments may be composed of two single chains, a VL-CL module and a VH-CH module. Alternatively, each of the individual Fab fragments may be arranged in a single chain, preferably, VL-CL-CH-VH, and the individual variable and constant domains may be connected with a peptide linker. In general, the individual single chains and Fab fragments may be connected via disulfide bonds, adhesive domains, chemically linked and/or peptide linker. The bispecific molecule may also comprise more than two Fab fragments, in particular, the molecule may be a Fab3, Fab4, or a multimeric Fab complex with specificity for 2, 3, 4, or more different antigens. The invention also includes chemically linked Fabs.

In one embodiment, the binding agent according to the invention includes various types of bivalent and trivalent single-chain variable fragments (scFvs), fusion proteins mimicking the variable domains of two antibodies. A single-chain variable fragment (scFv) is a fusion protein of the variable regions of the heavy (VH) and light chains (VL) of immunoglobulins, connected with a short linker peptide often to about 25 amino acids. The linker is usually rich in glycine for flexibility, as well as serine or threonine for solubility, and can either connect the N-terminus of the VH with the C-terminus of the VL, or vice versa. Divalent (or bivalent) single-chain variable fragments (di-scFvs, bi-scFvs) can be engineered by linking two scFvs. This can be done by producing a single peptide chain with two VH and two VL regions, yielding tandem scFvs. The invention also includes multispecific molecules comprising more than two scFvs binding domains. This makes it possible that the molecule comprises either multiple antigen specificities and is a trispecific, tetraspecific, or multispecific molecule, or the molecule is a bispecific molecule comprising more than one scFv binding domain with specificity for the same antigen. In particular, the molecule of the invention may be a multispecific single chain Fv.

Another possibility is the creation of scFvs with linker peptides that are too short for the two variable regions to fold together (about five amino acids), forcing scFvs to dimerize. This type is known as diabodies. Still shorter linkers (one or two amino acids) lead to the formation of trimers, so-called triabodies or tribodies. Tetrabodies have also been produced. They exhibit an even higher affinity to their targets than diabodies.

A particularly preferred example of a bispecific antibody fragment is a diabody (Kipriyanov, Int. J. Cancer 77 (1998), 763-772), which is a small bivalent and bispecific antibody fragment. Diabodies comprise a heavy chain variable domain (VH) connected to a light chain variable domain (VL) on the same polypeptide chain (VH-VL) connected by a peptide linker that is too short to allow pairing between the two domains on the same chain. This forces pairing with the complementary domains of another chain and promotes the assembly of a dimeric molecule with two functional antigen binding sites. To construct bispecific diabodies, the V-domains of e.g. an anti-CD3 antibody and an anti-tumor antigen antibody may be fused to create the two chains VH(CD3)-VL(tumor antigen), VH(tumor antigen)-VL(CD3). Each chain by itself is not able to bind to the respective antigen, but recreates the functional antigen binding sites on pairing with the other chain. To this end, a peptide linker that is too short to allow pairing between the two domains on the same chain is used. The two scFv molecules, with a linker between heavy chain variable domain and light chain variable domain that is too short for intramolecular dimerization, are co-expressed and self-assemble to form bi-specific molecules with the two binding sites at opposite ends.

According to another particularly preferred aspect, the bispecific binding agent of the invention is in the format of a bispecific single chain antibody construct, whereby said construct comprises or consists of at least two binding domains, whereby one of said domains binds to CD3 and a second domain binds to another antigen, e.g. a tumor antigen. Such molecules, also termed "bispecific T cell engagers" (BiTEs; the term BiTE only refers to bi-specific molecules of which one arm is specific for CD3) consist of two scFv molecules connected via a linker peptide.

As used herein, a "bispecific single chain antibody" denotes a single polypeptide chain comprising two binding domains. Each binding domain comprises one variable region from an antibody heavy chain ("VH region"), wherein the VH region of the first binding domain specifically binds to CD3, and the VH region of the second binding domain specifically binds to another antigen, e.g. a tumor antigen. The two binding domains are optionally linked to one another by a short polypeptide spacer. Each binding domain may additionally comprise one variable region from an antibody light chain ("VL region"), the VH region and VL region within each of the first and second binding domains being linked to one another via a polypeptide linker long enough to allow the VH region and VL region of the first binding domain and the VH region and VL region of the second binding domain to pair with one another.

The term "binding" according to the invention preferably relates to a specific binding.

According to the present invention, an agent such as an antibody is capable of binding to a predetermined target if it has a significant affinity for said predetermined target and binds to said predetermined target in standard assays. "Affinity" or "binding affinity" is often measured by equilibrium dissociation constant ($K_D$). Preferably, the term "significant affinity" refers to the binding to a predetermined target with a dissociation constant ($K_D$) of $10^{-5}$ M or lower, $10^{-6}$ M or lower, $10^{-7}$ M or lower, $10^{-8}$ M or lower, $10^{-9}$ M or lower, $10^{-10}$ M or lower, $10^{-11}$ M or lower, or $10^{-12}$ M or lower.

An agent is not (substantially) capable of binding to a target if it has no significant affinity for said target and does not bind significantly, in particular does not bind detectably, to said target in standard assays. Preferably, the agent does not detectably bind to said target if present in a concentration of up to 2, preferably 10, more preferably 20, in particular 50 or 100 µg/ml or higher. Preferably, an agent has no significant affinity for a target if it binds to said target with a $K_D$ that is at least 10-fold, 100-fold, $10^3$-fold, $10^4$-fold, $10^5$-fold, or $10^6$-fold higher than the $K_D$ for binding to the predetermined target to which the agent is capable of binding. For example, if the $K_D$ for binding of an agent to the target to which the agent is capable of binding is $10^{-7}$ M, the $K_D$ for binding to a target for which the agent has no significant affinity would be at least $10^{-6}$ M, $10^{-5}$ M, $10^{-4}$ M, $10^{-3}$ M, $10^{-2}$ M, or $10^{-1}$ M.

An agent such as an antibody is specific for a predetermined target if it is capable of binding to said predetermined target while it is not capable of binding to other targets, i.e. has no significant affinity for other targets and does not significantly bind to other targets in standard assays. According to the invention, an agent is specific for CD3 if it is capable of binding to CD3 but is not (substantially) capable of binding to other targets. Preferably, an agent is specific for CD3 if the affinity for and the binding to such other targets does not significantly exceed the affinity for or binding to CD3-unrelated proteins such as bovine serum albumin (BSA), casein, human serum albumin (HSA) or non-claudin transmembrane proteins such as MHC molecules or transferrin receptor or any other specified polypeptide. Preferably, an agent is specific for a predetermined target if it binds to said target with a $K_D$ that is at least 10-fold, 100-fold, $10^3$-fold, $10^4$-fold, $10^5$-fold, or $10^6$-fold lower than the $K_D$ for binding to a target for which it is not specific. For example, if the $K_D$ for binding of an agent to the target for which it is specific is $10^{-7}$ M, the $K_D$ for binding to a target for which it is not specific would be at least $10^{-6}$ M, $10^{-5}$ M, $10^{-4}$ M, $10^{-3}$ M, $10^{-2}$ M, or $10^{-1}$ M.

Binding of an agent to a target can be determined experimentally using any suitable method; see, for example, Berzofsky et al., "Antibody-Antigen Interactions" in Fundamental Immunology, Paul, W. E., Ed., Raven Press New York, N.Y. (1984), Kuby, Janis Immunology, W. H. Freeman and Company New York, N.Y. (1992), and methods described herein. Affinities may be readily determined using conventional techniques, such as by equilibrium dialysis; by using surface plasmon resonance analytic (e.g. Biacore), using general procedures outlined by the manufacturer; by radioimmunoassay using radiolabeled target antigen; or by another method known to the skilled artisan. The affinity data may be analyzed, for example, by the method of Scatchard et al., Ann N.Y. Acad. ScL, 51:660 (1949). The measured affinity of a particular antibody-antigen interaction can vary if measured under different conditions, e.g., salt concentration, pH. Thus, measurements of affinity and other antigen-binding parameters, e.g., $K_D$, $IC_{50}$, are preferably made with standardized solutions of antibody and antigen, and a standardized buffer.

The peptide mimotopes or binding agents described herein or nucleic acids encoding such peptide mimotopes or binding agents may be recombinant and/or isolated molecules.

The term "recombinant" in the context of the present invention means "made through genetic engineering". Preferably, a "recombinant object" such as a recombinant nucleic acid in the context of the present invention is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

An "isolated molecule" as used herein, is intended to refer to a molecule which is substantially free of other molecules such as other cellular material (e.g., an isolated antibody that specifically binds to CD3 is substantially free of antibodies that specifically bind antigens other than CD3).

It is to be understood that the peptide mimotopes and/or binding agents described herein may be delivered to a patient by administering a nucleic acid such as RNA encoding the peptide mimotope and/or binding agent and/or by administering a host cell comprising a nucleic acid such as RNA encoding the peptide mimotope and/or binding agent. Thus, a nucleic acid encoding a peptide mimotope and/or binding agent when administered to a patient may be present in naked form or in a suitable delivery vehicle such as in the form of liposomes or viral particles, or within a host cell. The nucleic acid provided can produce the peptide mimotope and/or binding agent over extended time periods in a sustained manner. Nucleic acids to be delivered to a patient can be produced by recombinant means. If a nucleic acid is administered to a patient without being present within a host cell, it is preferably taken up by cells of the patient for expression of the peptide mimotope and/or binding agent encoded by the nucleic acid. If a nucleic acid is administered to a patient while being present within a host cell, it is preferably expressed by the host cell within the patient so as to produce the peptide mimotope and/or binding agent encoded by the nucleic acid.

The term "nucleic acid", as used herein, is intended to include DNA and RNA such as genomic DNA, cDNA, mRNA, recombinantly produced and chemically synthesized molecules. A nucleic acid may be single-stranded or double-stranded. RNA includes in vitro transcribed RNA (IVT RNA) or synthetic RNA.

Nucleic acids may be comprised in a vector. The term "vector" as used herein includes any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

In the context of the present invention, the term "RNA" relates to a molecule which comprises ribonucleotide residues and preferably being entirely or substantially composed of ribonucleotide residues. "Ribonucleotide" relates to a nucleotide with a hydroxyl group at the 2'-position of a β-D-ribofuranosyl group. The term includes double stranded RNA, single stranded RNA, isolated RNA such as partially purified RNA, essentially pure RNA, synthetic RNA, recombinantly produced RNA, as well as modified RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

According to the present invention, the term "RNA" includes and preferably relates to "mRNA" which means "messenger RNA" and relates to a "transcript" which may be produced using DNA as template and encodes a peptide or protein. mRNA typically comprises a 5' non translated region (5'-UTR), a protein or peptide coding region and a 3' non translated region (3'-UTR). mRNA has a limited half-time in cells and in vitro. Preferably, mRNA is produced by in vitro transcription using a DNA template. In one embodiment of the invention, the RNA is obtained by in vitro transcription or chemical synthesis. The in vitro transcription methodology is known to the skilled person. For example, there is a variety of in vitro transcription kits commercially available.

In one embodiment of the present invention, RNA is self-replicating RNA, such as single stranded self-replicating RNA. In one embodiment, the self-replicating RNA is single stranded RNA of positive sense. In one embodiment, the self-replicating RNA is viral RNA or RNA derived from viral RNA. In one embodiment, the self-replicating RNA is alphaviral genomic RNA or is derived from alphaviral genomic RNA. In one embodiment, the self-replicating RNA is a viral gene expression vector. In one embodiment, the virus is Semliki forest virus. In one embodiment, the self-replicating RNA contains one or more transgenes at least one of said transgenes encoding the peptide mimotope/binding agent described herein. In one embodiment, if the RNA is viral RNA or derived from viral RNA, the transgenes may partially or completely replace viral sequences such as viral sequences encoding structural proteins. In one embodiment, the self-replicating RNA is in vitro transcribed RNA.

In order to increase expression and/or stability of the RNA used according to the present invention, it may be modified, preferably without altering the sequence of the expressed peptide or protein.

The term "modification" in the context of RNA as used according to the present invention includes any modification of RNA which is not naturally present in said RNA.

In one embodiment of the invention, the RNA used according to the invention does not have uncapped 5'-triphosphates. Removal of such uncapped 5'-triphosphates can be achieved by treating RNA with a phosphatase.

The RNA according to the invention may have modified naturally occurring or synthetic ribonucleotides in order to increase its stability and/or decrease cytotoxicity. For example, in one embodiment, in the RNA used according to the invention 5-methylcytidine is substituted partially or completely, preferably completely, for cytidine. Alternatively or additionally, in one embodiment, in the RNA used according to the invention pseudouridine is substituted partially or completely, preferably completely, for uridine.

In one embodiment, the term "modification" relates to providing an RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap (m7G). In the context of the present invention, the term "5'-cap" includes a 5'-cap analog that resembles the RNA cap structure and is modified to possess the ability to stabilize RNA if attached thereto, preferably in vivo and/or in a cell.

Providing an RNA with a 5'-cap or 5'-cap analog may be achieved by in vitro transcription of a DNA template in the presence of said 5'-cap or 5'-cap analog, wherein said 5'-cap is co-transcriptionally incorporated into the generated RNA strand, or the RNA may be generated, for example, by in vitro transcription, and the 5'-cap may be attached to the RNA post-transcriptionally using capping enzymes, for example, capping enzymes of vaccinia virus.

The RNA may comprise further modifications. For example, a further modification of the RNA used in the present invention may be an extension or truncation of the naturally occurring poly(A) tail or an alteration of the 5'- or 3'-untranslated regions (UTR) such as introduction of a UTR which is not related to the coding region of said RNA, for example, the insertion of one or more, preferably two copies of a 3'-UTR derived from a globin gene, such as alpha2-globin, alpha1-globin, beta-globin, preferably beta-globin, more preferably human beta-globin.

Therefore, in order to increase stability and/or expression of the RNA used according to the present invention, it may be modified so as to be present in conjunction with a poly-A sequence, preferably having a length of 10 to 500, more preferably 30 to 300, even more preferably 65 to 200 and especially 100 to 150 adenosine residues. In an especially preferred embodiment the poly-A sequence has a length of approximately 120 adenosine residues. In addition, incorporation of two or more 3'-non translated regions (UTR) into the 3'-non translated region of an RNA molecule can result in an enhancement in translation efficiency. In one particular embodiment the 3'-UTR is derived from the human β-globin gene.

Preferably, RNA if delivered to, i.e. transfected into, a cell, in particular a cell present in vivo, expresses the protein or peptide it encodes.

The term "transfection" relates to the introduction of nucleic acids, in particular RNA, into a cell. For purposes of the present invention, the term "transfection" also includes the introduction of a nucleic acid into a cell or the uptake of a nucleic acid by such cell, wherein the cell may be present in a subject, e.g., a patient. Thus, according to the present invention, a cell for transfection of a nucleic acid described herein can be present in vitro or in vivo, e.g. the cell can form part of an organ, a tissue and/or an organism of a patient. According to the invention, transfection can be transient or stable. For some applications of transfection, it is sufficient if the transfected genetic material is only transiently expressed. Since the nucleic acid introduced in the transfection process is usually not integrated into the nuclear genome, the foreign nucleic acid will be diluted through mitosis or degraded. Cells allowing episomal amplification of nucleic acids greatly reduce the rate of dilution. If it is desired that the transfected nucleic acid actually remains in the genome of the cell and its daughter cells, a stable transfection must occur. RNA can be transfected into cells to transiently express its coded protein.

The term "stability" of RNA relates to the "half-life" of RNA. "Half-life" relates to the period of time which is needed to eliminate half of the activity, amount, or number of molecules. In the context of the present invention, the half-life of an RNA is indicative for the stability of said RNA. The half-life of RNA may influence the "duration of expression" of the RNA. It can be expected that RNA having a long half-life will be expressed for an extended time period.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector".

The term "translation" according to the invention relates to the process in the ribosomes of a cell by which a strand of messenger RNA directs the assembly of a sequence of amino acids to make a peptide or protein.

The term "expression" is used according to the invention in its most general meaning and comprises the production of RNA and/or peptides or proteins, e.g. by transcription and/or translation. With respect to RNA, the term "expression" or "translation" relates in particular to the production of peptides or proteins. It also comprises partial expression of nucleic acids. Moreover, expression can be transient or stable. According to the invention, the term expression also includes an "aberrant expression" or "abnormal expression".

"Aberrant expression" or "abnormal expression" means according to the invention that expression is altered, preferably increased, compared to a reference, e.g. a state in a subject not having a disease associated with aberrant or abnormal expression of a certain protein, e.g., a tumor antigen. An increase in expression refers to an increase by at least 10%, in particular at least 20%, at least 50% or at least 100%, or more.

The term "specifically expressed" means that a protein is essentially only expressed in a specific tissue or organ. For example, a tumor antigen specifically expressed in gastric mucosa means that said protein is primarily expressed in gastric mucosa and is not expressed in other tissues or is not expressed to a significant extent in other tissue or organ types. Thus, a protein that is exclusively expressed in cells of the gastric mucosa and to a significantly lesser extent in any other tissue, such as testis, is specifically expressed in cells of the gastric mucosa.

According to the invention, the term "RNA encoding" means that RNA, if present in the appropriate environment, preferably within a cell, can be expressed to produce a protein or peptide it encodes.

The term "peptide" according to the invention comprises oligo- and polypeptides and refers to substances comprising two or more, preferably 3 or more, preferably 4 or more, preferably 6 or more, preferably 8 or more, preferably 9 or more, preferably 10 or more, preferably 13 or more, preferably 16 more, preferably 21 or more and up to preferably 8, 10, 20, 30, 40 or 50, in particular 100 amino acids joined covalently by peptide bonds. The term "protein" refers to large peptides, preferably to peptides with more than 100 amino acid residues, but in general the terms "peptides" and "proteins" are synonyms and are used interchangeably herein.

According to the invention, a peptide may include natural amino acids and non-natural amino acids. In one embodiment, a peptide merely includes natural amino acids.

According to the invention, the term "non-natural amino acid" refers to an amino acid having a structure different from those of the 20 natural amino acid species. Since non-natural amino acids have structures similar to those of natural amino acids, non-natural amino acids may be classified as derivatives or analogs of given natural amino acids.

According to the invention, the term "cyclization" or "cyclic peptide" relates to a peptide or polypeptide chain which forms a ring, preferably to a peptide or polypeptide having an intramolecular bond between two non-adjacent amino acids within a peptide. The intramolecular bond includes, but is not limited to, backbone to backbone, side-chain to backbone and side-chain to side-chain cyclizations. A peptide can be cyclized in four different ways: head-to-tail (C-terminus to N-terminus), head-to-side chain, side chain-to-tail or side-chain-to-side-chain. Furthermore, a cyclized peptide of the invention may form a bridging group comprising, for example, a disulfide, amide, lactone, triazole, thioether, thioester, imine, ether, ester or an alkene. The amino acids involved in the formation of such bridging group may for example have a functional group selected from amine, thiol, oxy, hydroxyl, carboxy, aldehyde, azide, alkyne, alkene, chloroalkyl, bromoalkyl, and iodoalkyl. Particularly preferred according to the invention are peptides containing two or more residues containing thiol groups such as cysteines which can form intramolecular disulfide bridges giving cyclic peptides. Cys-Cys cyclization results from the formation of disulfide bridges between cysteine residues of the peptide such as between the amino acids at positions 2 and 10 of the amino acid sequences described herein. However, according to the invention, an intramolecular bond may be formed in a peptide described herein by a cyclization which is different from a Cys-Cys cyclization. Thus, in one embodiment, the present invention also envisions peptides, wherein one or both of the Cys residues in the peptides described herein are replaced by (a) residue(s) other than Cys. Thus, in one embodiment, one or both of the Cys residues at positions 2 and 10 of the amino acid sequences described herein may be replaced by (an) amino acid(s) which is (are) able to form an intramolecular bond in the peptide. Preferably, said bond is formed between the amino acids at positions 2 and 10 of the amino acid sequences described herein.

According to the invention, a peptide mimotope may be covalently or non-covalently bound to one or more other compounds. Such compounds include peptidic compound such as peptides and proteins as well as non-peptidic compounds such as polyethylene glycol (PEG).

In one embodiment, the peptide mimotopes described herein are PEGylated. PEGylation is the process of covalent attachment of polyethylene glycol (PEG) polymer chains to another molecule, such as a peptide or protein. The covalent attachment of PEG can "mask" the agent from the host's immune system (reduced immunogenicity and antigenicity), and increase the hydrodynamic size (size in solution) of the agent which prolongs its circulatory time by reducing renal clearance. PEGylation can also provide water solubility to hydrophobic drugs and proteins.

The teaching given herein with respect to specific amino acid sequences, e.g. those shown in the sequence listing, is to be construed so as to also relate to variants of said specific sequences resulting in sequences which are functionally equivalent to said specific sequences, e.g. amino acid sequences exhibiting properties identical or similar to those of the specific amino acid sequences. One important property is to retain binding to a target.

It will be appreciated by those skilled in the art that in particular the sequences of the CDR, hypervariable and variable regions can be modified without losing the ability to bind to a target. For example, CDR regions will be either identical or highly homologous to the regions of antibodies specified herein. By "highly homologous" it is contemplated that from 1 to 5, preferably from 1 to 4, such as 1 to 3 or 1 or 2 substitutions may be made in the CDRs. In addition, the hypervariable and variable regions may be modified so that they show substantial homology with the regions of antibodies specifically disclosed herein.

For the purposes of the present invention, "variants" of an amino acid sequence comprise amino acid insertion variants, amino acid addition variants, amino acid deletion variants and/or amino acid substitution variants. Amino acid deletion variants that comprise the deletion at the N-terminal and/or C-terminal end of the protein are also called N-terminal and/or C-terminal truncation variants.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise amino- and/or carboxy-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. The deletions may be in any position of the protein.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

Preferably the degree of similarity, preferably identity between a given amino acid sequence and an amino acid sequence which is a variant of said given amino acid sequence will be at least about 60%, 65%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

The term "percentage identity" is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

The term "cell" or "host cell" preferably relates to an intact cell, i.e. a cell with an intact membrane that has not released its normal intracellular components such as enzymes, organelles, or genetic material. An intact cell preferably is a viable cell, i.e. a living cell capable of carrying out its normal metabolic functions. Preferably said term relates according to the invention to any cell which can be transfected with an exogenous nucleic acid. Preferably, the cell when transfected with an exogenous nucleic acid can express the nucleic acid.

"Reduce", "decrease" or "inhibit" as used herein means an overall decrease or the ability to cause an overall decrease, preferably of 5% or greater, 10% or greater, 20% or greater, more preferably of 50% or greater, and most preferably of 75% or greater, in the level, e.g. in the level of expression or in the level of proliferation of cells.

Terms such as "increase" or "enhance" preferably relate to an increase or enhancement by about at least 10%, preferably at least 20%, preferably at least 30%, more preferably at least 40%, more preferably at least 50%, even more preferably at least 80%, and most preferably at least 100%, at least 200%, at least 500%, at least 1000%, at least 10000% or even more.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality. According to the invention, the term "disease" includes cancer, in particular those forms of cancer described herein. Any reference herein to cancer or particular forms of cancer also includes cancer metastasis thereof. In a preferred embodiment, a cancer to be treated according to the present application involves cells expressing a tumor antigen.

"Cancer involving cells expressing a tumor antigen" or similar expressions means according to the invention that a tumor antigen is expressed in cells of a diseased tissue or organ affected with cancer such as in cancer cells, preferably on the surface of said cells. In one embodiment, expression of a tumor antigen in cells of a diseased tissue or organ is increased compared to the state in a healthy tissue or organ. An increase refers to an increase by at least 10%, in particular at least 20%, at least 50%, at least 100%, at least 200%, at least 500%, at least 1000%, at least 10000% or even more. In one embodiment, expression is only found in a diseased tissue or organ, while expression in a healthy tissue or organ is repressed.

"Cell surface" is used in accordance with its normal meaning in the art, and thus includes the outside of the cell which is accessible to binding by proteins and other molecules A tumor antigen is expressed on the surface of cells if it is located at the surface of said cells and is accessible to binding by tumor antigen-specific antibodies added to the cells.

The terms "cancer disease" or "cancer" refer to or describe the physiological condition in an individual that is typically characterized by unregulated cell growth. Examples of cancers include, but are not limited to, carcinoma, lymphoma, blastoma, sarcoma, and leukemia. More particularly, examples of such cancers include bone cancer, blood cancer, lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma.

The term "cancer" according to the invention also comprises cancer metastases. Preferably, a "cancer disease" is characterized by cells expressing a tumor antigen and a cancer cell expresses a tumor antigen. A cell expressing a tumor antigen preferably is a cancer cell, preferably of the cancers described herein.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system. In one embodiment, the term "metastasis" according to the invention relates to lymph node metastasis. One particular form of metastasis which is treatable using the therapy of the invention is metastasis originating from gastric cancer as primary site. In preferred embodiments such gastric cancer metastasis is Krukenberg tumors, peritoneal metastasis and/or lymph node metastasis.

Krukenberg tumor is an uncommon metastatic tumor of the ovary accounting for 1% to 2% of all ovarian tumors. Prognosis of Krukenberg tumor is still very poor and there is no established treatment for Krukenberg tumors. Krukenberg tumor is a metastatic signet ring cell adenocarcinoma of the ovary. Stomach is the primary site in most Krukenberg tumor cases (70%). Carcinomas of colon, appendix, and breast (mainly invasive lobular carcinoma) are the next most common primary sites. Rare cases of Krukenberg tumor originating from carcinomas of the gallbladder, biliary tract, pancreas, small intestine, ampulla of Vater, cervix, and urinary bladder/urachus have been reported.

The term "treatment" or "therapeutic treatment" relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The terms "prophylactic treatment" or "preventive treatment" relate to any treatment that is intended to prevent a disease from occurring in an individual. The terms "prophylactic treatment" or "preventive treatment" are used herein interchangeably.

The terms "immunization" or "vaccination" describe the process of administering an antigen to an individual with the purpose of inducing an immune response, for example, for therapeutic or prophylactic reasons.

The terms "protect", "prevent", "prophylactic", "preventive", or "protective" relate to the prevention and/or treatment of the occurrence and/or the propagation of a disease, e.g. tumor, in an individual. For example, a prophylactic administration of a therapy can protect the receiving individual from the development of a disease.

The terms "individual" and "subject" are used herein interchangeably. They refer to human beings, non-human primates or other mammals (e.g. mouse, rat, rabbit, dog, cat, cattle, swine, sheep, horse or primate) that can be afflicted with or are susceptible to a disease or disorder (e.g., cancer) but may or may not have the disease or disorder. In many embodiments, the individual is a human being. Unless otherwise stated, the terms "individual" and "subject" do not denote a particular age, and thus encompass adults, elderlies, children, and newborns. In preferred embodiments of the present invention, the "individual" or "subject" is a "patient". The term "patient" means according to the invention a subject for treatment, in particular a diseased subject.

"Target cell" shall mean any undesirable cell such as a cancer cell. In preferred embodiments, the target cell expresses a tumor antigen.

The term "antigen" relates to an agent comprising an epitope against which an immune response is to be generated and/or is directed. The term "antigen" includes in particular proteins, peptides, polysaccharides, nucleic acids, especially RNA and DNA, and nucleotides. The term "antigen" also includes agents, which become antigenic—and sensitizing—only through transformation (e.g. intermediately in the molecule or by completion with body protein). An antigen or a processing product thereof is preferably recognizable by a T or B cell receptor, or by an immunoglobulin molecule such as an antibody. In a preferred embodiment, the antigen is a disease-associated antigen, such as a tumor antigen, a viral antigen, or a bacterial antigen.

In the context of the present invention, the term "tumor antigen" or "tumor-associated antigen" preferably relates to proteins that are under normal conditions specifically expressed in a limited number of tissues and/or organs or in specific developmental stages and are expressed or aberrantly expressed in one or more tumor or cancer tissues. In the context of the present invention, the tumor-associated antigen is preferably associated with the cell surface of a cancer cell and is preferably not or only rarely expressed in normal tissues. The term "tumor antigen" includes claudin 18.2 (CLDN18.2) and claudin 6 (CLDN6).

CLDN18.2 and CLDN6 have been identified as differentially expressed in tumor tissues, with the only normal tissues expressing CLDN18.2 being stomach and the only normal tissue expressing CLDN6 being placenta.

CLDN18.2 is selectively expressed in normal tissues in differentiated epithelial cells of the gastric mucosa. CLDN18.2 is expressed in cancers of various origins such as pancreatic carcinoma, esophageal carcinoma, gastric carcinoma, bronchial carcinoma, breast carcinoma, and ENT tumors. CLDN18.2 is a valuable target for the prevention and/or treatment of primary tumors, such as gastric cancer, esophageal cancer, pancreatic cancer, lung cancer such as non small cell lung cancer (NSCLC), ovarian cancer, colon cancer, hepatic cancer, head-neck cancer, and cancers of the gallbladder, and metastases thereof, in particular gastric cancer metastasis such as Krukenberg tumors, peritoneal metastasis, and lymph node metastasis.

CLDN6 has been found to be expressed, for example, in ovarian cancer, lung cancer, gastric cancer, breast cancer, hepatic cancer, pancreatic cancer, skin cancer, melanomas, head neck cancer, sarcomas, bile duct cancer, renal cell cancer, and urinary bladder cancer. CLDN6 is a particularly preferred target for the prevention and/or treatment of ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, breast cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, testicular embryonal carcinoma, placental choriocarcinoma, cervical cancer, testicular cancer, in particular testicular seminoma, testicular teratoma and embryonic testicular cancer, uterine cancer, germ cell tumors such as a teratocarcinoma or an embryonal carcinoma, in particular germ cell tumors of the testis, and the metastatic forms thereof.

The term "CLDN18.2" preferably relates to human CLDN18.2, and, in particular, to a protein comprising, preferably consisting of the amino acid sequence according to SEQ ID NO: 6 of the sequence listing or a variant of said amino acid sequence. The first extracellular loop of CLDN18.2 preferably comprises amino acids 27 to 81, more preferably amino acids 29 to 78 of the amino acid sequence shown in SEQ ID NO: 6. The second extracellular loop of CLDN18.2 preferably comprises amino acids 140 to 180 of the amino acid sequence shown in SEQ ID NO: 6. Said first and second extracellular loops preferably form the extracellular portion of CLDN18.2.

The term "CLDN6" preferably relates to human CLDN6, and, in particular, to a protein comprising, preferably consisting of the amino acid sequence of SEQ ID NO: 7 or SEQ ID NO: 8 of the sequence listing or a variant of said amino acid sequence. The first extracellular loop of CLDN6 preferably comprises amino acids 28 to 80, more preferably amino acids 28 to 76 of the amino acid sequence shown in SEQ ID NO: 7 or the amino acid sequence shown in SEQ ID NO: 8. The second extracellular loop of CLDN6 preferably comprises amino acids 138 to 160, preferably amino acids 141 to 159, more preferably amino acids 145 to 157 of the amino acid sequence shown in SEQ ID NO: 7 or the amino acid sequence shown in SEQ ID NO: 8. Said first and second extracellular loops preferably form the extracellular portion of CLDN6.

The term "variant" according to the invention refers, in particular, to mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence. The term "variant" shall encompass any posttranslationally modified variants and conformation variants.

The agents such as peptide mimotopes described herein may be administered in the form of any suitable pharmaceutical composition.

The pharmaceutical compositions of the invention are preferably sterile and contain an effective amount of the agents described herein and optionally of further agents as discussed herein to generate the desired reaction or the desired effect.

Pharmaceutical compositions are usually provided in a uniform dosage form and may be prepared in a manner known per se. A pharmaceutical composition may e.g. be in the form of a solution or suspension.

A pharmaceutical composition may comprise salts, buffer substances, preservatives, carriers, diluents and/or excipients all of which are preferably pharmaceutically acceptable. The term "pharmaceutically acceptable" refers to the non-toxicity of a material which does not interact with the action of the active component of the pharmaceutical composition.

Salts which are not pharmaceutically acceptable may be used for preparing pharmaceutically acceptable salts and are included in the invention. Pharmaceutically acceptable salts of this kind comprise in a non-limiting way those prepared from the following acids: hydrochloric, hydrobromic, sulfuric, nitric, phosphoric, maleic, acetic, salicylic, citric, formic, malonic, succinic acids, and the like. Pharmaceutically acceptable salts may also be prepared as alkali metal salts or alkaline earth metal salts, such as sodium salts, potassium salts or calcium salts.

Suitable buffer substances for use in a pharmaceutical composition include acetic acid in a salt, citric acid in a salt, boric acid in a salt and phosphoric acid in a salt.

Suitable preservatives for use in a pharmaceutical composition include benzalkonium chloride, chlorobutanol, paraben and thimerosal.

An injectable formulation may comprise a pharmaceutically acceptable excipient such as Ringer Lactate.

The term "carrier" refers to an organic or inorganic component, of a natural or synthetic nature, in which the active component is combined in order to facilitate, enhance or enable application. According to the invention, the term "carrier" also includes one or more compatible solid or liquid fillers, diluents or encapsulating substances, which are suitable for administration to a patient.

Possible carrier substances for parenteral administration are e.g. sterile water, Ringer, Ringer lactate, sterile sodium chloride solution, polyalkylene glycols, hydrogenated naphthalenes and, in particular, biocompatible lactide polymers, lactide/glycolide copolymers or polyoxyethylene/polyoxypropylene copolymers.

The term "excipient" when used herein is intended to indicate all substances which may be present in a pharmaceutical composition and which are not active ingredients such as, e.g., carriers, binders, lubricants, thickeners, surface active agents, preservatives, emulsifiers, buffers, flavouring agents, or colorants.

The agents and compositions described herein are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition.

An effective amount of an agent or composition described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a patient is insufficient with an initial dose, higher doses (or effectively higher doses achieved by a different, more localized route of administration) may be used.

The agents and compositions described herein can be administered to patients, e.g., in vivo, to treat or prevent a variety of disorders such as those described herein. Preferred patients include human patients having disorders that can be corrected or ameliorated by administering the agents and compositions described herein. This includes disorders involving cells characterized by an altered expression pattern of a tumor antigen.

For example, in one embodiment, agents described herein can be used to treat a patient with a cancer disease, e.g., a cancer disease such as described herein characterized by the presence of cancer cells expressing a tumor antigen.

The pharmaceutical compositions and methods of treatment described according to the invention may also be used for immunization or vaccination to prevent a disease described herein.

The pharmaceutical composition of the invention may be administered together with supplementing immunity-enhancing substances such as one or more adjuvants and may comprise one or more immunity-enhancing substances to further increase its effectiveness, preferably to achieve a synergistic effect of immunostimulation. The term "adjuvant" relates to compounds which prolongs or enhances or accelerates an immune response. Various mechanisms are possible in this respect, depending on the various types of adjuvants. For example, compounds which allow the maturation of the DC, e.g. lipopolysaccharides or CD40 ligand, form a first class of suitable adjuvants. Generally, any agent which influences the immune system of the type of a "danger signal" (LPS, GP96, dsRNA etc.) or cytokines, such as GM-CSF, can be used as an adjuvant which enables an immune response to be intensified and/or influenced in a controlled manner. CpG oligodeoxynucleotides can optionally also be used in this context, although their side effects which occur under certain circumstances, as explained above, are to be considered. Particularly preferred adjuvants are cytokines, such as monokines, lymphokines, interleukins or chemokines, e.g. IL-1, IL-2, IL-3, IL-4, IL-5, IL-6, IL-7, IL-8, IL-9, IL-10, IL-12, INFα, INF-γ, GM-CSF, LT-α, or growth factors, e.g. hGH. Further known adjuvants are aluminium hydroxide, Freund's adjuvant or oil such as Montanide®, most preferred Montanide® ISA51. Lipopeptides, such as Pam3Cys, are also suitable for use as adjuvants in the pharmaceutical composition of the present invention.

The pharmaceutical composition can be administered locally or systemically, preferably systemically.

The term "systemic administration" refers to the administration of an agent such that the agent becomes widely distributed in the body of an individual in significant amounts and develops a desired effect. For example, the agent may develop its desired effect in the blood and/or reaches its desired site of action via the vascular system.

Typical systemic routes of administration include administration by introducing the agent directly into the vascular system or oral, pulmonary, or intramuscular administration wherein the agent is adsorbed, enters the vascular system, and is carried to one or more desired site(s) of action via the blood.

According to the present invention, it is preferred that the systemic administration is by parenteral administration. The term "parenteral administration" refers to administration of an agent such that the agent does not pass the intestine. The term "parenteral administration" includes intravenous administration, subcutaneous administration, intradermal administration or intraarterial administration but is not limited thereto.

The present invention is further illustrated by the following examples which are not be construed as limiting the scope of the invention.

EXAMPLES

Example 1. Materials and Methods

Phage Display Selection:

TR66 binding peptides were identified by phage display technology using a Ph.D.™-C7C phage display peptide library kit (New England Biolabs) with a solution-phase panning protocol. For the panning 50 µl of Protein A Dynabeads (Invitrogen) were at first washed once with 1 ml of TBS-T buffer (50 mM Tris-HCl (pH 7.5), 150 mM NaCl+0.1% Tween-20) and subsequently blocked with 1 ml blocking buffer (3% BSA in TBS) for 1 h at 4° C. Afterwards, the beads were washed four times with 1 ml TBS-T buffer. A 100-fold representation of the library (1E+11 phages) was incubated with 100 nM of the antibody for 20 min at RT. Antibody-bound phages were captured with blocked Protein A beads by incubation for 15 min at RT with slight shaking. After incubation, beads were washed ten times with TBS-T to remove unbound phages. Elution was done by subsequent incubation with 50 µl of 100 mM triethylamine (for 6 min) and 50 µl of 100 mM glycine-HCl, pH 2 (for 10 min). Eluates were combined and immediately neutralized with 100 µl 1 M Tris-HCl, pH 7. Amplification of the neutralized phages was done according to manufacturer's instructions by infection of log-phase ER2738 $E.$ $coli$ cells. Amplified phages were purified from $E.$ $coli$ supernatant also as described in the NEB manual by double PEG precipitation. Purified phages were quantified photometrically and used for subsequent panning rounds. Two additional screening rounds were done with decreased antibody concentration (50 nM) and increased washing stringency (washing with 0.5% Tween). To analyse enrichment, phage solutions were titrated before the panning (input) and after elution (output). Furthermore, the pools from round 1-3 were analysed for target binding in an indirect phage ELISA. Therefore, 10 µg of the TR66 antibody were coated per well of a Nunc Maxisorp plate in 50 mM $Na_2CO_3$ pH 9.4. Afterwards, wells were blocked overnight at 4° C. with 300 µl 5% milkpowder in TBS buffer. After washing twice with 300 µl TBS buffer per well, incubation with 1E+12 phages per well (100 µl per well, diluted with 0.5% milkpowder in TBS) was done for 90 min at 4° C. Wells were washed three times with TBS-T and twice with TBS. Afterwards, bound phages were detected with HRP conjugated anti-M13 antibody (GE Healthcare, 1:5000 diluted with 0.5% milkpowder in TBS) and 3,3',5,5'-Tetramethylbenzidine (TMB) substrate.

Single Phage Clone Analysis:

After the third screening round, individual phage clones were generated and tested for target binding in a direct phage ELISA. For this purpose, 1E+11 phages were coated to a 96 well Maxisorp™ plate (Thermo Fisher Scientific) in coating buffer (50 mM sodium carbonate, pH 9.4) for 1 h at 37° C. Eight separate wells were coated per clone. The liquid was discarded and wells were blocked overnight at 4° C. with 300 µl blocking buffer (5% milkpowder in TBS buffer). After washing twice with 300 µl TBS buffer per well, incubation with 500 nM TR66 (100 µl per well, diluted with 0.5% milkpowder in TBS) was done for 90 min at 4° C. Wells were washed three times with TBS-T and twice with TBS. Afterwards, bound antibody was detected with HRP conjugated goat anti-human IgG antibody (Sigma-Aldrich, 1:5000 diluted with 0.5% milkpowder in TBS) and TMB substrate. As a control, reactions without the first antibody (TR66) were performed. For sequence analysis phage DNA was isolated using the QIAprep Spin M13 kit (Qiagen).

Peptide Optimization with Peptide Microarrays:

Peptides were synthesized and printed on peptide-microarray slides essentially as described previously (Funkner, A. et al., J. Mol. Biol. 425, 1340-1362 (2013)). In brief, the peptides were synthesized using SPOT synthesis (Wenschuh, H. et al., Biopolymers 55, 188-206 (2000)) cleaved from the solid support and cyclized (50% DMSO, PBS buffer pH 7-8, RT, 16 hours). Subsequently, all peptides were chemoselectively immobilized on functionalized glass slides as described earlier (Schnatbaum, K. et al., Biotechnol. J. 9, 545-554 (2014); Funkner, A. et al., J. Mol. Biol. 425, 1340-1362 (2013)). Each peptide was deposited on the microarray in triplicates.

The microarrays were incubated with 1.0 or 0.1 µg/ml TR66 in an HS 4800 microarray processing station (Tecan) for two hours at 30° C., followed by incubation with 1.0 µg/ml fluorescently labelled secondary antibody (Alexa647 anti-human Fc antibody; Jackson Immuno Research). Washing steps were performed prior every incubation step with 0.1% Tween-20 in 1xTBS. After the final incubation step the microarrays were washed (0.05% Tween-20 in 0.1xSSC) and dried in a stream of nitrogen. Each microarray was scanned using a GenePix Autoloader 4200AL (Molecular Devices, Pixel size: 10 m). Signal intensities were evaluated using GenePix Pro 7.0 analysis software (Molecular Devices). For each peptide, the mean of the three triplicates was calculated.

Further evaluation of results was performed using the statistical computing and graphics software R (Version 2.15.2, www.r-project.org).

Synthesis of Purified Peptides:

The peptides were synthesized by standard Fmoc-based solid-phase-synthesis protocols and purified. All target peptides were obtained with a purity of >80%.

Binding Analysis Using Peptide ELISA:

For the detection of TR66 or OKT3 (Bio-X-Cell), the CD3 mimicking peptides were immobilized on streptavidin plates (Nunc) in a concentration of 0.75 µg/ml in PBS buffer for 1 hour at 37° C. Subsequently, the plate was washed three times with washing buffer (0.01% Tween-20 in PBS buffer) before it was blocked with 3% BSA in PBS overnight at 4° C. To detect TR66 or OKT3, the blocked plate was washed again three times with washing buffer followed by the addition of TR66 or OKT3 and incubation for 30 min at 37° C. After another washing step, it was incubated with an alkaline phosphatase conjugated Goat anti-human or anti-mouse IgG, Fc antibody (Jackson Immuno Research) for additional 30 min at 37° C. Finally, the plate was washed again before being incubated with 1.5 mg/ml of the substrate PNPP (para-nitrophenyl phosphate) in appropriate substrate buffer (1 M Diethanolamine, 0.05 mM $MgCl_2$, 0.01% sodium azide, pH 9.8) for 30 min at RT in the dark. 3 M KOH was used to stop the enzymatic reaction. Absorbance was measured with a microplate reader (Infinite M200, Tecan). For dual wavelength analysis, 405 nm was chosen as measurement wavelength and 492 nm as reference wavelength. Absorbance values were calculated by subtraction of the measured values for the reference wavelength and for the measurement wavelength. Calculation of apparent KD values was done by fitting the data with Sigma Plot 10 using a two-site saturation binding model.

Binding Analysis Using Biolayer Interferometry:

Binding analysis was performed using streptavidin (SA) sensors on an Octet Red system (fortéBIO). 5 µg/ml of biotinylated peptides were used for loading (200 µl per sensor). To prevent unspecific binding 1× blocking buffer (Sigma-Aldrich) was used in each step after loading. Remained biotin binding sites on coated streptavidin sensors were blocked using 100 µg/ml biocytin (Sigma-Aldrich) for 5 minutes. For binding mode analysis of different peptides 500 nM TR66 antibody was used in the association step. For detailed analysis the antibody was used in a range of 1.5625 to 100 nM (1.5625, 3.125, 6.25, 12.5, 25, 50, 100 nM) for each analyzed peptide. The following program was used:

Baseline: 1000 rpm for 180 sec.

Load: 1000 rpm for 900 sec.

Baseline: 1000 rpm for 180 sec.

Blocking: 1000 rpm for 300 sec.

Association: 1000 rpm for 1200-2400 sec.

Dissociation: 1000 rpm for 1200-2400 sec.

Example 2. Selection of TR66-Specific Peptides by Phage Display

For the identification of CD3 T-cell co-receptor epsilon chain mimetic peptides phage display was performed using a disulfide-constrained random 7 mer M13 phage library (New England Biolabs) and a CD3ε specific antibody (clone TR66). To ensure good accessibility of the antibody a selection in solution protocol with protein-A bead capture of binding phages was carried out. After three consecutive screening rounds with increased stringency an enrichment of target-specific phages could be observed, measured by dilution plating of input and output phages (Table 1) and an indirect phage ELISA (FIG. 1).

TABLE 1

Enrichment of phages for each round of selection.

| Round | Input | Output | Ratio Input/Output |
|---|---|---|---|
| 1 | E+12 | 5.2E+7 | 1.9E+4 |
| 2 | 1.2E+11 | 1.4E+8 | 8.3E+2 |
| 3 | 5.25E+11 | 1.4E+8 | 3.62E+3 |

The shown values are derived from titering the phage pools before each panning round (input) and the eluted phages (output). The decreasing ratio of input/output indicates an enrichment of phages.

Figure 2:
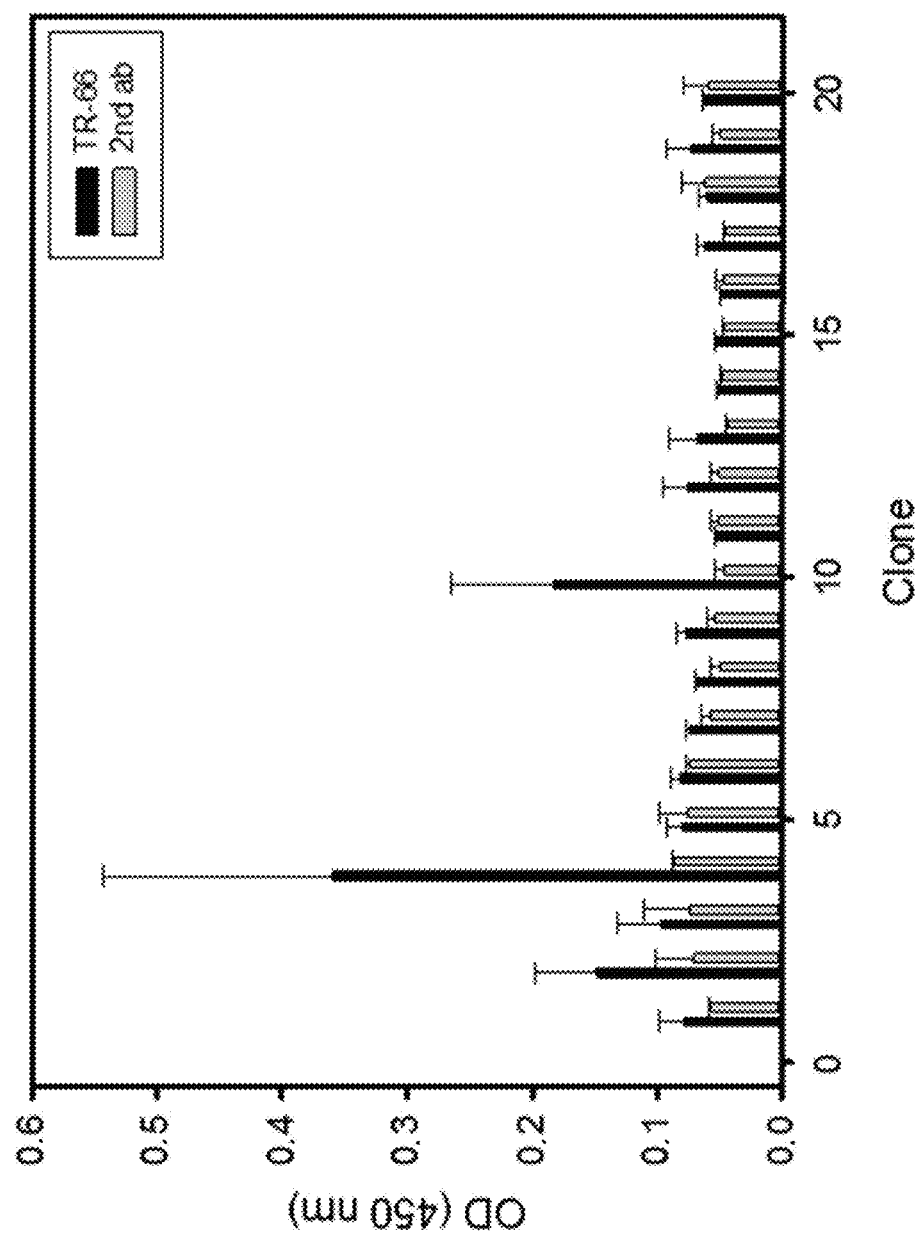
FIG. 2. Single clone analysis from TR66 phage screening. Phage ELISA binding analysis of 20 randomly picked clones from the $3^{rd}$ screening round. 1E+11 phages were coated to each well of a Maxisorp™ plate and subsequently incubated with TR66 antibody. Binding was detected with a HRP conjugated goat anti-human IgG antibody (Sigma) and the chromogenic substrate 3,3',5,5'-Tetramethylbenzidine (TMB). As a control, reactions without TR66 were performed ($2^{nd}$ ab). SD values are presented as error bars.
Figure 3:
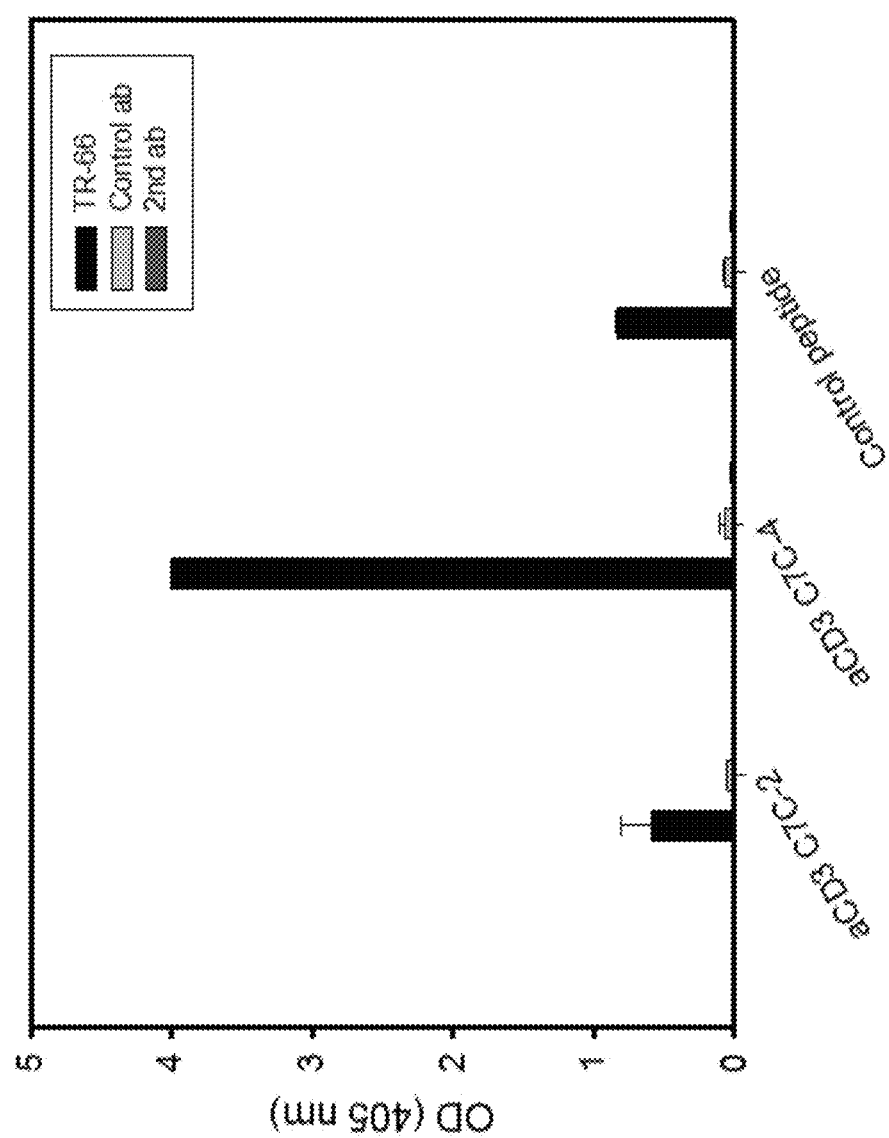
FIG. 3. Binding analysis of phage derived variants using a peptide based ELISA. Biotinylated peptides were immobilized on streptavidin plates (Nunc) in a concentration of 0.75 μg/ml. After blocking 30 μg/ml TR66 or an unrelated antibody (control ab) were added and incubated for 1 h at 37° C. Binding was detected with an alkaline phosphatase conjugated goat anti-human IgG antibody (Sigma) and the chromogenic substrate PNPP (para-nitrophenyl phosphate). All reactions were performed as duplicates. SD values are presented as error bars.

Analysis of 20 single clones randomly picked after the 3rd screening round yielded potential TR66 binders (FIG. 2), but only the binding of clone 4 (ACTRPGDPQCGGGS (SEQ ID NO: 29)) could be verified after chemical synthesis of the variants and ELISA-based binding analysis (FIG. 3). Therefore, clone 4 was selected for further binding and SAR analysis and optimization via peptide microarrays.

Example 3. SAR Analysis and Optimization of TR66-Specific Peptides by Peptide Microarrays Peptide microarrays were used for structure-activity-relationship (SAR) analysis and optimization of peptide binding affinity to TR66. For assay setup different variants of the cyclic hit peptide (aCD3 C7C-4) were prepared differing in a) the immobilization site, b) the linker nature and c) the degree of conformational restriction (cyclic vs. linear). All peptides were chemically synthesized in a stepwise fashion from the C- to the N-terminus by the high-throughput SPOT synthesis approach 19 applying a cellulose membrane as solid support. After cleavage and isolation, the peptides were cyclized through disulfide formation between two internal Cys residues and immobilized to the microarray. Covalent attachment to the microarray was performed through a reactive moiety on either the N- or C-terminus of the peptides allowing chemoselective and directed immobilization through both ends of the peptides. Subsequently, peptide loaded microarrays were incubated with 1.0 or 0.1 µg/ml TR66 followed by incubation with 1 µg/ml fluorescently labelled secondary antibody, scanning and data evaluation. The TR66 antibody exhibits strong binding to the parental (cyclic, immobilized through C-terminus) peptide (data not shown). As expected, reduction of the TR66 concentration to 0.1 µg/ml reduced the assay signal (data not shown).

Figure 4:
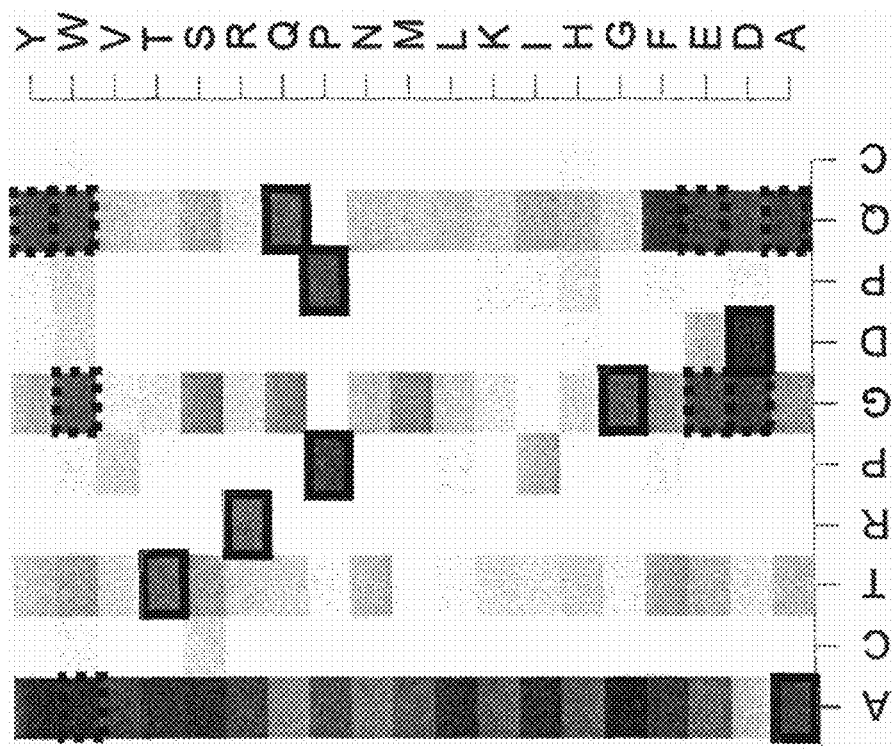
FIG. 4. SAR analysis of TR66 binding peptides using peptide microarrays. Shown are the results for the incubation of TR66 on peptide microarrays presenting substitutional analyses of the aCD3 C7C-4 variant. Following the primary incubation binding was detected as fluorescence intensity using a fluorescently labelled anti-human Fc antibody. Each amino acid of the starting sequence (shown at the bottom) is substituted by each of the other natural amino acids except Cys, resulting in an overall number of 8×19=152 different peptides. Dark colour represents strong signals, shades show weaker signals. The solid boxes indicate the amino acids of the original peptide. The peptides highlighted with dashed boxes were selected for re-synthesis, purification and detailed binding analysis. AU peptides are presented on the arrays in triplicates. Mean signal intensities from a representative of 3 independent experiments is shown.

After assay set-up experiments peptide optimization substitutional analyses (exchange of parental amino acids at each position by all proteinogenic amino acids except Cys) were performed using the C-terminal immobilization format. In total 152 peptides were synthesized, handled, cyclized and immobilized to microarrays as described above. The results after incubation of the peptide microarray with TR66 are shown in FIG. 4. It became apparent that substitution of most positions of the starting sequence resulted in decreased signal intensities. However, substitutions at position 1 (alanine), 6 (glycine) and 9 (glutamine) were tolerated. To some extend also threonine at position 3 could be exchanged. Several sequences showing highest signal intensities were selected for re-synthesis, purification and detailed binding analysis (FIG. 4, dashed boxes).

Example 4. Detailed Binding Analysis of Optimized TR66-Specific Peptides

The peptides displaying the highest binding affinities from the peptide microarray experiments were synthesized by standard Fmoc-based solid-phase-synthesis protocols and purified (HPLC purity: >80%). The binding characteristics of each peptide were determined. In the first instance all peptides were analysed via biolayer interferometry (BLI) to get a first impression whether the respective variant has a significant binding property at all (yes/no binding, Table 2). At his point, only one TR66 concentration (500 nM) was tested. Except variants aCD3-04-010 and aCD3-04-012 all peptides show a measurable binding activity.

TABLE 2

Binding characteristics of parental and maturated peptides.

| Peptide | Sequence[a] | Yes/no binding, BLI[c] | Apparent $K_D$, ELISA[b] [nM] |
|---|---|---|---|
| aCD3 C7C-4 | ACTRPGDPQC-GGGS-K(Bio) (SEQ ID NO: 19) | Yes | 370 |
| aCD3-04-002 | ACTRP<u>D</u>DPQC-GGGS-K(Bio) (SEQ ID NO: 20) | Yes | 78 |
| aCD3-04-006 | <u>W</u>CTRPGDPQC-GGGS-K(Bio) (SEQ ID NO: 21) | Yes | 226 |
| aCD3-04-007 | ACTRP<u>E</u>DPQC-GGGS-K(Bio) (SEQ ID NO: 22) | Yes | 299 |
| aCD3-04-008 | ACTRPGDP<u>A</u>C-GGGS-K(Bio) (SEQ ID NO: 23) | Yes | 164 |
| aCD3-04-009 | ACTRPGDP<u>Y</u>C-GGGS-K(Bio) (SEQ ID NO: 24) | Yes | 167 |
| aCD3-04-010 | ACTR<u>(NMI)</u>GDPQC-GGGS-K(Bio) (SEQ ID NO: 25) | No | – |
| aCD3-04-012 | ACTRP<u>W</u>DPQC-GGGS-K(Bio) (SEQ ID NO: 26) | No | – |
| aCD3-04-013 | ACTRP<u>D</u>DP<u>E</u>C-GGGS-K(Bio) (SEQ ID NO: 27) | Yes | 4 |
| aCD3-04-014 | ACTRP<u>DD</u>P<u>W</u>C-GGGS-K(Bio) (SEQ ID NO: 28) | Yes | 111 |

Shown are the amino acid sequences and the binding characteristics of each variant determined by biolayer interferometry (BLI) and ELISA.
[a]All peptides were cyclized by Cys-Cys-disulfide bond formation. K(Bio) indicates a lysine residue that carries a biotin moiety linked to the epsilon amino group. NMI: N-methylisoleucine. Amino acids that were exchanged compared to the original sequence are underlined.
[b]Shown values represent the mean of at least two individual measurements.
[c]Determined from BLI measurement using 500 nM TR66 antibody.

Figure 5:
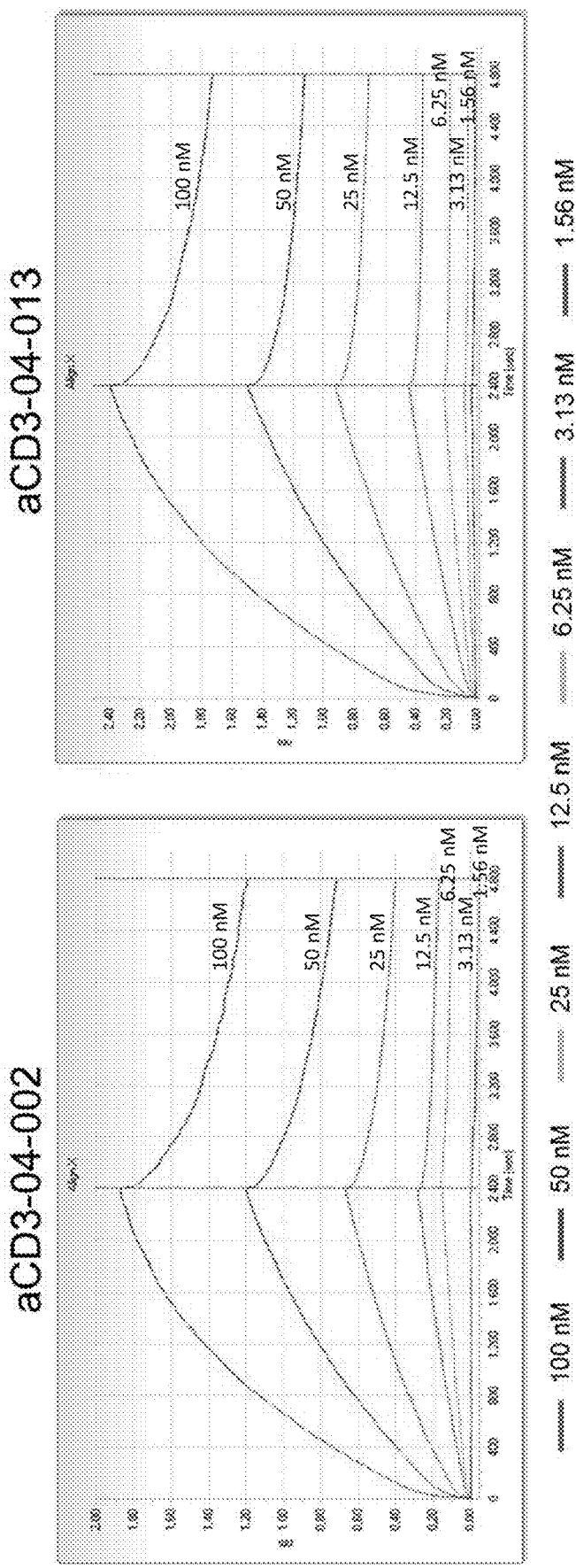
FIG. 5. Comparative binding analysis of matured TR66 mimotopes aCD3-04-002 and aCD3-04-013 using biolayer interferometry (BLI) on an Octet Red system (fortéBIO). Biotinylated peptides were immobilized onto streptavidin (SA) sensors. After blocking with 1× blocking buffer and biocytin association and dissociaten rates of TR66 binding were recorded over a period of 2400 sec respectively. The antibody was used in a range of 1.5625 to 100 nM (1.5625, 3.125, 6.25, 12.5, 25, 50, 100 nM) for each analyzed peptide.

Then, ELISA was used for assessment of the thermodynamic behaviour of the binding and to compare the peptides among themselves. The results of the measurements shown in Table 2 indicate that the affinity of the maturated variants could be significantly improved compared to the parental peptide (peptide aCD3 C7C-4). The apparent KD of the best variants, peptides aCD3-04-002 (ACTRPDDPQC-GGGS-K(Bio) (SEQ ID NO: 20)) and aCD3-04-013 (ACTRPDDPEC-GGGS-K(Bio) (SEQ ID NO: 27)), are approximately 5 or even 100 times lower. Both maturated mimotopes were also analysed in detail using BLI to assess the kinetic parameters (FIG. 5). Although a concentration-dependent binding could be observed in both cases, a concrete dissociation constant could unfortunately not be determined, because the data could not be fitted using the available models.

Figure 6:
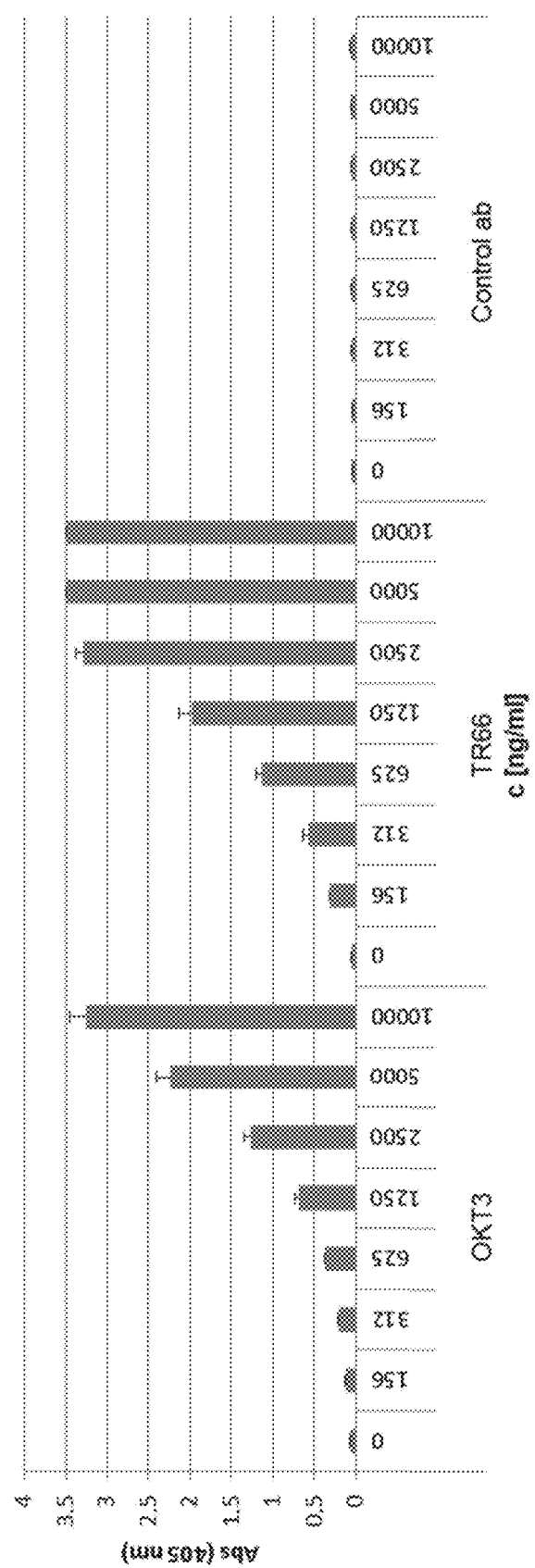
FIG. 6. Comparative binding analysis of maturated TR66 mimotope aCD3-04-013 to approved antibody Muromanab-CD3 (Orthoclone OKT3®). Biotinylated peptides were immobilized on streptavidin plates (Nunc). After blocking different concentrations (0, 156, 312, 625, 1250, 5000 and 10000 ng/ml) of TR66, OKT3 or an unrelated antibody (control ab) were added and incubated for 1 h at 37° C. Binding was detected with an alkaline phosphatase conjugated goat anti-human IgG antibody (Sigma) and the chromogenic substrate PNPP (para-nitrophenyl phosphate). All reactions were performed as duplicates. SD values are presented as error bars.

Muromonab-CD3 (Orthoclone OKT3®) is a murine CD3-specific monoclonal antibody which is approved for the therapy of acute, glucocorticoid-resistant rejection of allogeneic renal, heart and liver transplants (Emmons, C. & Hunsicker, L. G., Iowa Med. 77, 78-82 (1987); Reichert, J. M., MAbs. 4, 413-415 (2012)). To analyze whether the identified maturated mimotope aCD3-04-013 is cross-reactive to OKT3 an ELISA was performed (FIG. 6). Titration of OKT3 showed specific binding to TR66 mimotope aCD3-04-013 with slightly lower affinity compared to TR66 binding. This might be due to different detection antibodies used in this ELISA setup (TR66 has a human Fc part and OKT3 is murine).

The invention claimed is:

1. A peptide mimotope of CD3, which comprises the amino acid sequence:

(SEQ ID NO: 9)
Xaa1 Cys Thr Arg Pro Xaa2 Asp Pro Xaa3 Cys wherein
Xaa1 is any amino acid,
Xaa2 is any amino acid,
and Xaa3 is any amino acid.

2. The peptide mimotope of claim 1, which comprises an amino acid sequence selected from the group consisting of:

(SEQ ID NO: 10)
Ala Cys Thr Arg Pro Gly Asp Pro Gln Cys (SEQ ID NO: 11)
Trp Cys Thr Arg Pro Gly Asp Pro Gln Cys (SEQ ID NO: 12)
Ala Cys Thr Arg Pro Glu Asp Pro Gln Cys

-continued

```
                                           (SEQ ID NO: 13)
Ala Cys Thr Arg Pro Gly Asp Pro Ala Cys (SEQ ID NO: 14)
Ala Cys Thr Arg Pro Gly Asp Pro Tyr Cys (SEQ ID NO: 15)
Ala Cys Thr Arg Pro Asp Asp Pro Gln Cys (SEQ ID NO: 16)
Ala Cys Thr Arg Pro Trp Asp Pro Gln Cys (SEQ ID NO: 17)
Ala Cys Thr Arg Pro Asp Asp Pro Glu Cys and
                                           (SEQ ID NO: 18)
Ala Cys Thr Arg Pro Asp Asp Pro Trp Cys.
```

3. The peptide mimotope of claim 1, which comprises the amino acid sequence:

```
                                           (SEQ ID NO: 15)
Ala Cys Thr Arg Pro Gly Asp Pro Gln Cys.
```

4. The peptide mimotope of claim 1, which comprises the amino acid sequence:

```
                                           (SEQ ID NO: 10)
Ala Cys Thr Arg Pro Asp Asp Pro Gln Cys.
```

5. The peptide mimotope of claim 1, which comprises the amino acid sequence:
Ala Cys Thr Arg Pro Asp Asp Pro Glu Cys (SEQ ID NO: 17).

6. The peptide mimotope of claim 1, wherein the peptide mimotope is a structural mimic of either a linear or conformational CD3 epitope.

7. The peptide mimotope of claim 1, wherein the peptide mimotope is a structural mimic of an epitope in the extracellular domain of CD3.

8. The peptide mimotope of claim 1, which has a binding capacity to a CD3 binding domain and/or competes with CD3 for binding to a CD3 binding domain.

9. The peptide mimotope of claim 8, wherein the CD3 binding domain comprises a variable domain of a heavy chain of an immunoglobulin (VH) with a specificity for CD3 (VH(CD3)) and a variable domain of a light chain of an immunoglobulin (VL) with a specificity for CD3 (VL(CD3)).

10. The peptide mimotope of claim 9, wherein said VH(CD3) comprises an amino acid sequence represented by SEQ ID NO: 2 or a fragment thereof or a variant of said amino acid sequence or fragment and the VL(CD3) comprises an amino acid sequence represented by SEQ ID NO: 3 or a fragment thereof or a variant of said amino acid sequence or fragment.

11. The peptide mimotope of claim 8, wherein said binding is a specific binding.

12. The peptide mimotope of claim 1 further comprising at least one fusion partner.

13. The peptide mimotope of claim 12, wherein the fusion partner comprises a heterologous amino acid sequence.

14. The peptide mimotope of claim 12 further comprising at least one further moiety.

15. The peptide mimotope of claim 14, wherein the at least one further moiety is covalently associated with the amino acid sequence.

16. The peptide mimotope of claim 14, wherein the fusion partner or further moiety comprises a carrier protein, label, reporter, or tag.

17. A recombinant nucleic acid which encodes a peptide mimotope wherein the peptide mimotope comprises the amino acid sequence:
Xaa1 Cys Thr Arg Pro Xaa2 Asp Pro Xaa3 Cys (SEQ ID NO: 9)
wherein
Xaa1 is any amino acid,
Xaa2 is any amino acid,
and Xaa3 is any amino acid.

18. A host cell comprising a recombinant nucleic acid which encodes a peptide mimotope, wherein the peptide mimotope comprises the amino acid sequence:
Xaa1 Cys Thr Arg Pro Xaa2 Asp Pro Xaa3 Cys (SEQ ID NO: 9)
wherein
Xaa1 is any amino acid,
Xaa2 is any amino acid,
and Xaa3 is any amino acid.

19. A test kit comprising the peptide mimotope of claim 1.

20. An assay device comprising the peptide mimotope of claim 1.

21. The assay device of claim 20, wherein the peptide mimotope is releasably or non-releasably immobilised on a solid support.

22. A method for assaying for the presence and/or amount of CD3 in a sample comprising contacting the sample with the peptide mimotope of claim 1.

23. A method for assaying for the presence and/or amount of binding agents to CD3 in a sample comprising contacting the sample with the peptide mimotope of claim 1.

24. A method for capturing binding agents to CD3 in a sample comprising contacting the sample with the peptide mimotope of claim 1.

25. A method of purifying a CD3 binding agent, comprising a step of treating a sample comprising the CD3 binding agent with an immobilized peptide mimotope of claim 1, a washing step, and an elution step whereby purified CD3 binding agent is obtained.

26. A pharmaceutical composition comprising the peptide mimotope of claim 1.

27. A method of treating a subject in need thereof comprising administering to the subject a therapeutically effective amount of the peptide mimotope of claim 1.

28. The method of claim 27, wherein the subject is, will be or has been exposed to a CD3 binding agent.

29. The peptide mimotope of claim 1, wherein Xaa1 is an amino acid selected from the group consisting of Tyr, Trp, Val, Thr, Ser, Arg, Gln, Pro, Asn, Met, Leu, Lys, Ile, His, Gly, Phe, Glu, Asp, and Ala.

30. The peptide mimotope of claim 1, wherein Xaa1 is an amino acid selected from the group consisting of Tyr, Trp, Val, Thr, Ser, Arg, Gln, Pro, Asn, Met, Leu, Lys, Ile, His, Gly, Phe, Glu, and Ala.

31. The peptide mimotope of claim 1, wherein Xaa1 is an amino acid selected from the group consisting of Tyr, Trp, Val, Thr, Ser, Arg, Pro, Met, Leu, Lys, Ile, His, Gly, Phe, Glu, and Ala.

32. The peptide mimotope of claim 1, wherein Xaa1 is an amino acid selected from the group consisting of Tyr, Trp, Val, Thr, Ser, Arg, Pro, Leu, Ile, Gly, Phe, and Ala.

33. The peptide mimotope of claim 1, wherein Xaa2 is an amino acid selected from the group consisting of Gly, Asp, Glu, and Trp.

34. The peptide mimotope of claim 1, wherein Xaa2 is an amino acid selected from the group consisting of Gly, Asp, and Glu.

35. The peptide mimotope of claim 1, wherein Xaa3 is an amino acid selected from the group consisting of Gln, Tyr, Trp, Phe, Glu, Asp, and Ala.

36. A method for assaying for the presence and/or amount of CD3 antibodies in a sample comprising contacting the sample with the peptide mimotope of claim 1.

37. A method for capturing CD3 antibodies in a sample comprising contacting the sample with the peptide mimotope of claim 1.

38. A method of purifying a CD3 binding agent, comprising a step of treating a sample comprising the CD3 binding agent with an immobilized peptide mimotope of claim 1, a washing step, and an elution step whereby purified CD3 binding agent is obtained.

\* \* \* \* \*